(12) United States Patent
Amtmann et al.

(10) Patent No.: US 10,953,099 B2
(45) Date of Patent: Mar. 23, 2021

(54) COMPOSITIONS COMPRISING A METAL SOURCE, DITHIOCARBAMATE AND CYCLODEXTRIN

(71) Applicant: DEUTSCHES KREBSFORSCHUNGSZENTRUM STIFTUNG DES ÖFFENTLICHEN RECHTS, Heidelberg (DE)

(72) Inventors: Eberhard Amtmann, Heidelberg (DE); Nikolas Gunkel, Heidelberg (DE); Aubry Miller, Heidelberg (DE); Michael Morgen, Valwig (DE)

(73) Assignee: DEUTSCHES KREBSFORSCHUNGSZENTRUM STIFTUNG DES ÖFFENTLICHEN RECHTS, Heidelberg (DE)

( * ) Notice: Subject to any disclaimer, the term of this patent is extended or adjusted under 35 U.S.C. 154(b) by 0 days.

(21) Appl. No.: 16/335,520

(22) PCT Filed: Oct. 13, 2017

(86) PCT No.: PCT/EP2017/076242
§ 371 (c)(1),
(2) Date: Mar. 21, 2019

(87) PCT Pub. No.: WO2018/069525
PCT Pub. Date: Apr. 19, 2018

(65) Prior Publication Data
US 2019/0328886 A1 Oct. 31, 2019

(30) Foreign Application Priority Data
Oct. 13, 2016 (EP) ..................................... 16193797

(51) Int. Cl.
| | |
|---|---|
| *A61K 47/40* | (2006.01) |
| *A61P 35/00* | (2006.01) |
| *A61K 31/28* | (2006.01) |
| *A61P 35/02* | (2006.01) |
| *A61K 33/243* | (2019.01) |
| *A61K 31/27* | (2006.01) |
| *A61K 31/555* | (2006.01) |
| *A61K 31/7048* | (2006.01) |
| *C07F 1/00* | (2006.01) |

(52) U.S. Cl.
CPC .............. *A61K 47/40* (2013.01); *A61K 31/27* (2013.01); *A61K 31/28* (2013.01); *A61K 31/555* (2013.01); *A61K 31/7048* (2013.01); *A61K 33/243* (2019.01); *A61P 35/00* (2018.01); *A61P 35/02* (2018.01); *C07F 1/005* (2013.01)

(58) Field of Classification Search
None
See application file for complete search history.

(56) References Cited

U.S. PATENT DOCUMENTS

| 6,288,110 B1 | 9/2001 | Marikovsky |
| 6,548,540 B2 | 4/2003 | Kennedy |

FOREIGN PATENT DOCUMENTS

| EP | 2238978 A1 | 10/2010 |
| JP | 2002-348238 A | 12/2002 |
| WO | 01/17522 A1 | 3/2001 |
| WO | 2009/117333 A1 | 9/2009 |
| WO | 2012/076897 A1 | 6/2012 |
| WO | 2015/120254 A1 | 8/2015 |

OTHER PUBLICATIONS

International Search Report and Written Opinion issued in International Application No. PCT/EP2017/076242, dated Dec. 7, 2017, 21 pages.
Nicolas Charlier et al., "Evaluation of lipid-based carrier systems and inclusion complexes of diethyldithiocarbamate-iron to trap nitric oxide in biological systems," Magnetic Resonance in Medicine, vol. 55, No. 1, 2005, pp. 215-218.
Alex Fragoso et al., "Influence of Positively-Charged Guests on the Superoxide Dismutase Mimetic Activity of Copper(II)β-Cyclodextrin Dithiocarbamates," Journal of Carbohydrate Chemistry, vol. 16, No. 2, 1997, pp. 171-180.
Ayyappa Bathinapatla et al., "Fabrication of copper nanoparticles decorated multiwalled carbon nanotubes as a high performance electrochemical sensor for the detection of neotame," Biosensors and Bioelectronics, vol. 67, 2015, pp. 200-207.
Loftsson T et al., "Evaluation of cyclodextrin solubilization of drugs," International Journal of Pharmaceutics, Elsevier, NL, vol. 302, No. 1-2, 2005, pp. 18-28.
Xia Zhang et al., "Inhibition of Tumor Proteasome Activity by Gold-Dithiocarbamato Complexes via Both Redox-Dependent and -Independent Processes," Journal of Cellular Biochemistry, vol. 1 No. 1, 2009, pp. 162-172.
Karen Brown et al., "197Au Moessbauer Spectroscopic Data for Antiarthritic Drugs and Related Gold(I) Thiol Derivatives," J. Am. Chem. SOC, Macromolecules Chem. Phys. Lett, 1981, pp. 4943-4945.

(Continued)

*Primary Examiner* — Joseph R Kosack
(74) *Attorney, Agent, or Firm* — Hamre, Schumann, Mueller & Larson, P.C.

(57) ABSTRACT

The present invention provides a novel class of dithiocarbamate-metal complexes and their uses in medicine. Also provided by the invention are combinations and pharmaceutical compositions, comprising a dithiocarbamate (or thiuram disulphide) such as disulfiram and cyclodextrin, with a source of a heavy metal. Surprisingly, the inventors found a synergistic potentiation of the anti-tumor effect, when a dithiocarbamate/heavy metal mixture was combined with a cyclodextrin. The compounds and combination of the invention are particularly useful in the treatment of tumor diseases, and other disorders. Provided are the compounds, combination, pharmaceutical compositions and kits, as well as methods for the preparation of the combinations of the invention.

5 Claims, 17 Drawing Sheets

(56) References Cited

OTHER PUBLICATIONS

Figure 1:
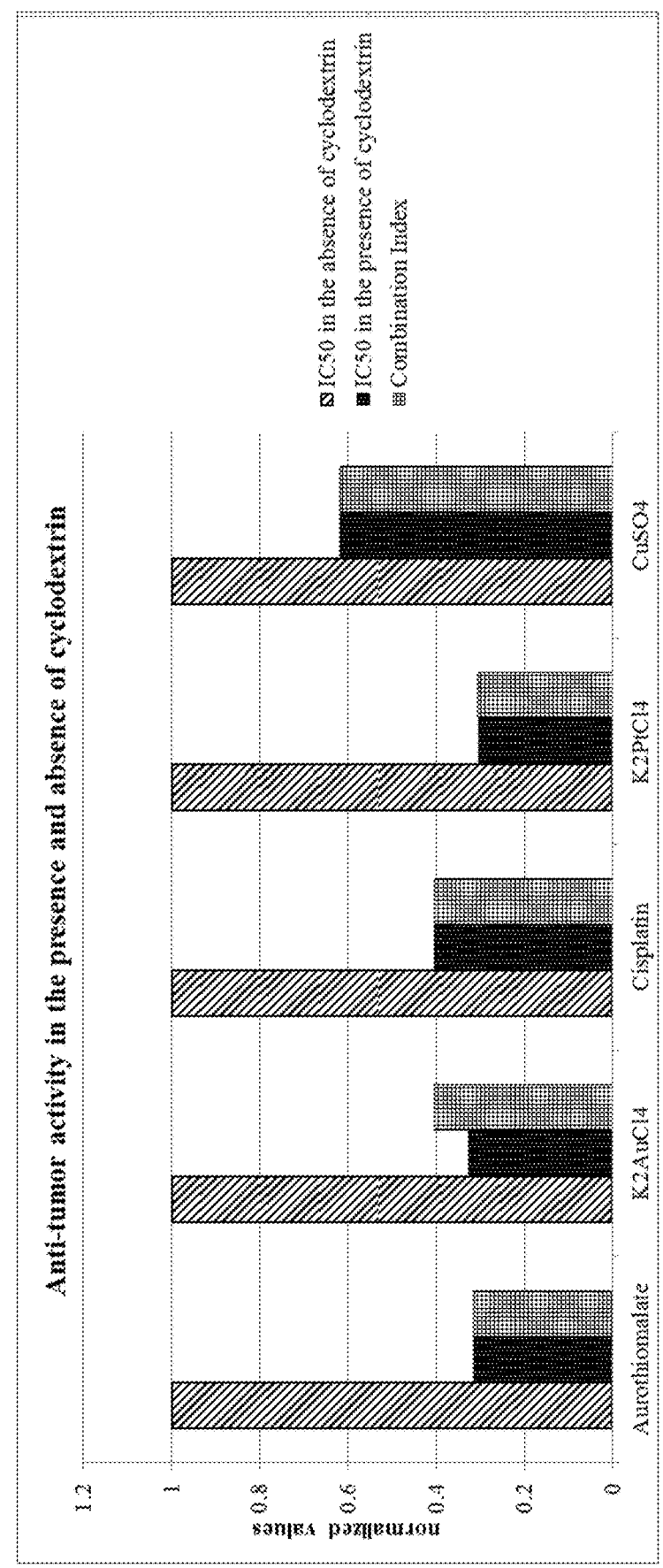

Luca Ronconi et al., "Gold Dithiocarbamate Derivatives as Potential Antineoplastic Agents: Design, Spectroscopic Properties, and in Vitro Antitumor Activity," Inorganic Chemistry, vol. 44, No. 6, 2005, pp. 1867-1881.

Giulia Boscutti et al., "Insights into the Reactivity of Gold-Dithiocarbamato Anticancer Agents toward Model Biomolecules by Using Multinuclear NMR Spectroscopy," Chemistry—A European Journal, vol. 19, No. 40, 2013, pp. 13428-13436.

Hogarth Graeme, "Metal-dithiocarbamate complexes: chemistry and biological activity," Mini Reviews In Medicinal Chemistry, Bentham Science Publishers, NL, vol. 12, No. 12, 2012, pp. 1202-1215.

Joseph Weinstock et al., "Oral Gold. Synthesis and Antiarthritic Poperties of Some Large-Ring Gold Chelates," Journal of Medicinal Chemistry, vol. 17, No. 1, 1974, pp. 139-140.

A

B

C

B

C

D

A:

| | H209 | H1882 | H1105 | H69 | H146 | A549 | LUTC-ML-54 | LX-289 | HaCat | SCLC MW | SCLC SD | NSCLC MW | NSCLC SD | NSCLC/ SCLC | HaCat/ SCLC | T-test |
|---|---|---|---|---|---|---|---|---|---|---|---|---|---|---|---|---|
| DKFZ-00610 | 0,11 | 0,10 | 0,16 | 0,11 | 0,20 | 11,82 | 7,61 | 26,70 | 14,69 | 0,14 | 0,04 | 15,38 | 10,03 | 113,74 | 108,68 | 0,01 |
| DKFZ-00608 | 0,08 | 0,04 | 0,07 | 0,09 | 0,09 | 6,49 | 6,48 | 23,40 | 13,44 | 0,08 | 0,02 | 12,12 | 9,77 | 159,80 | 177,18 | 0,01 |
| Auranofin | 0,10 | 0,03 | 0,33 | 0,41 | 0,65 | 1,35 | 2,62 | 1,98 | 2,87 | 0,30 | 0,25 | 1,98 | 0,64 | 6,53 | 9,46 | 0,00 |
| P-AuDTC | 0,03 | 0,06 | 0,31 | 0,42 | 0,10 | 0,81 | 2,30 | 0,95 | 2,81 | 0,18 | 0,17 | 1,35 | 0,83 | 7,39 | 15,34 | 0,01 |
| MC3 | 0,10 | 0,71 | 2,60 | 1,91 | 0,23 | 0,13 | 0,09 | 5,38 | 7,98 | 1,11 | 1,10 | 1,87 | 3,04 | 1,69 | 7,21 | 0,31 |
| Cisplatin | 1,02 | 2,51 | 0,41 | 10,23 | 10,00 | 8,43 | | 25,19 | 6,84 | 4,89 | 4,89 | 11,21 | 12,82 | 2,32 | 1,42 | 0,17 |
| Au12 | 25,67 | 45,14 | 3,04 | 100,34 | 77,44 | 122,98 | | 156,31 | 69,44 | 50,33 | 39,07 | 139,64 | 23,56 | 2,77 | 1,38 | 0,02 |
| DKFZ-00613 | 0,02 | 0,04 | 0,03 | 0,06 | 0,04 | 9,70 | 0,75 | 10,35 | 2342,00 | 0,04 | 0,01 | 6,82 | 4,20 | 181,78 | 61,30 | 0,03 |
| DKFZ-00614 | 1,58 | 5,14 | 8,19 | 10,26 | 26,95 | 506,00 | 134,32 | 219,90 | 80,52 | 10,42 | 8,76 | 284,00 | 164,52 | 27,20 | 7,72 | 0,03 |
| DKFZ-00615 | 0,07 | 0,15 | 0,25 | 0,28 | 0,59 | 22,46 | 2,51 | 2,51 | 5,56 | 0,27 | 0,18 | 15,49 | 9,00 | 57,20 | 20,53 | 0,01 |

B:

C:

C:

COMPOSITIONS COMPRISING A METAL SOURCE, DITHIOCARBAMATE AND CYCLODEXTRIN

FIELD OF THE INVENTION

The present invention provides a novel class of dithiocarbamate-metal complexes and their uses in medicine. Also provided by the invention are combinations and pharmaceutical compositions, comprising a dithiocarbamate (or thiuram disulphide) such as disulfiram and cyclodextrin, with a source of a heavy metal. Surprisingly, the inventors found a synergistic potentiation of the anti-tumor effect, when a dithiocarbamate/heavy metal mixture was combined with a cyclodextrin. The compounds and combination of the invention are particularly useful in the treatment of tumor diseases, and other disorders. Provided are the compounds, combination, pharmaceutical compositions and kits, as well as methods for the preparation of the combinations of the invention.

DESCRIPTION

Cancer, the uncontrolled growth of malignant cells, is a major health problem of the modern medical era. While some malignancies, such as adenocarcinoma of the breast and lymphomas such as Hodgkin's Disease, respond relatively well to current chemotherapeutic antineoplastic drug regimens, other cancers are poorly responsive to chemotherapy, especially melanoma, non-small cell lung, pancreatic, liver, prostate and colon cancers. Even small cell cancer of the lung, initially chemotherapy sensitive, tends to return after remission, with widespread metastatic spread leading to death of the patient. Thus, better treatment approaches are needed for these illnesses.

Dithiocarbamates or thiuram disulfides such as tetraethylthiuram disulfide, hereinafter called disulfiram, are chelators of heavy metals and used as a therapeutic agent. Disulfiram for example is the active ingredient in the drug Antabuse® used for many years in aversion therapy for chronic alcoholism. Disulfiram also has the potential to be used as a treatment for neoplastic diseases (Wickstrom, Danielsson et al. 2007, Conticello, Martinetti et al. 2012, Triscott, Rose Pambid et al. 2015). U.S. Pat. No. 6,288,110, entitled, "Pharmaceutical compositions comprising disulfiram," discloses disulfiram to inhibit angiogenesis and to be useful in the treatment of angiogenesis-dependent disorders, including neoplasms, and to prevent cell hyperproliferation and formation of clots along or around medical devices. The entire contents of which are incorporated herein by reference.

Phenotypically, disulfiram induces apoptosis, (Wang, Zhai et al. 2011) inhibits cell proliferation, and reduces angiogenesis, (Shian, Kao et al. 2003) thereby reducing invasion and metastasis. (Hothi, Martins et al. 2012, Duan, Xiao et al. 2014). The molecular mechanisms underlying these phenotypic effects are complex as disulfiram appears to inhibit multiple targets (Trapp, Lee et al. 2009; Sauna, Peng et al. 2004; Zhao, Xiao et al. 2015; Brar, Grigg et al. 2004; Yakisich, Siden et al. 2001; Chen, Cui et al. 2006; Cho, Lee et al. 2007; Li, Yang et al. 2008; Zhang, Chen et al. 2010; Xu, Shi et al. 2011; Yip, Fombon et al. 2011; Liu, Brown et al. 2012; Zha, Chen et al. 2014). This might be the reason why disulfiram is effective in heterogeneous preclinical models like breast, prostate, myeloma, leukemia, melanoma, neuroblastoma, colorectal cancer, cervix adenocarcinoma and lung cancers (Wang, McLeod et al. 2003, Lin, Haffner et al. 2011; Ketola, Kallioniemi et al. 2012; Morrison, Doudican et al. 2010; Lovborg, Oberg et al. 2006; Wickstrom, Danielsson et al. 2007; Yakisich, Siden et al. 2001, Brar, Grigg et al. 2004).

International publication WO 2015/120254 A1 describes the use of disulfiram in the treatment of brain tumors due to the activity of disulfiram in complex with a metal ion to inhibit the 06-methylguanine DNA methyltransferase. Moreover, when used in conjunction with metals like copper (Allensworth, Evans et al. 2015), gold (Huang, Liao et al. 2016), cadmium (Li, Yang et al. 2008) and zinc (Wiggins, Wymant et al. 2015) the action of disulfiram could be enhanced to various extends. U.S. Pat. No. 6,548,540, entitled, "Method of treating cancer using dithiocarbamate derivatives," discloses dithiocarbamate, particularly disulfiram, and thiocarbamate anions strongly inhibit the growth of cancer cells of a variety of cell types. Such inhibitory effect is enhanced by heavy metal ions such as copper ions, cytokines and ceruloplasmin and a method is presented for using disulfiram to reduce tumor growth, and to potentiate the effect of other anticancer agents. The entire contents of which are incorporated herein by reference. Disulfiram per se was shown to increases the efficacy of chemotherapeutics like cisplatin (Kadia and Shah 2016), 5FU (Wang, McLeod et al. 2003), doxorubicin (Xu, Shi et al. 2011), sunitinib (Ketola, Kallioniemi et al. 2012), docetaxel (Budman and Calabro 2002), paclitaxel (Yip, Fombon et al. 2011), gemcitabine (Guo, Xu et al. 2010) and temozolomide (Zhao, Xiao et al. 2015) in cellular cancer models. Disulfiram was also shown to be effective in animal models (Allensworth, Evans et al. 2015; Liu, Wang et al. 2016; Brar, Grigg et al. 2004; Chen, Cui et al. 2006), albeit at significantly higher doses as compared to the in vitro models. This restricted in vivo efficacy is also reflected by the fact that only one of the clinical trials completed so far reported encouraging outcomes. (Nechushtan, Hamamreh et al. 2015). The discrepancy between in vitro cytotoxicity and anticancer efficacy in patients is likely to be caused by the rapid degradation of disulfiram in the gastrointestinal system, hepatic first-pass effect and rapid metabolism in the blood stream (Johansson 1992) which limits the therapeutic amount of drug reaching the cancer, thus presenting a major hurdle for successful clinical use of disulfiram in cancer treatment. The international publication WO 2012076897 A1 describes a disulfiram formulation comprising disulfiram or a derivative thereof together with a component that increases the in vivo half-life of the disulfiram or the derivative thereof, and uses thereof, in particular the use with or without a separate copper formulation for the treatment of cancer. In addition to its pharmacokinetic limitations, disulfiram is a reactive compound which readily forms complexes with combination partners, in particular metals. The resulting reaction products (Hogarth 2012) show reduced solubility (Wehbe, Anantha et al. 2016) and increased serum albumin binding (Christodoulou, Sadler et al. 1995). Currently, clinical useable pharmaceutical formulations containing disulfiram and copper, or any other heavy metal have not been described, hampering its use in clinical settings.

Before the present invention is described, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

The above problem is solved by a combination comprising the components: Dithiocarbamate and cyclodextrin. The combination of the invention in some embodiments preferably further comprises a source for a heavy metal. In other preferred embodiments of the invention the dithiocarbamate and the source of a heavy metal is provided as a "dithiocarbamate metal chelate", which is a compound that has a heavy metal bonded to a dithiocarbamate thiolate anion. The mode of bonding can vary, which can include covalent and/or non-covalent (e.g., electrostatic, hydrogen bonding, dipole-dipole, dative bonding, etc.). Surprisingly the combination of a dithiocarbamate/heavy metal complex with cyclodextrin resulted in a significant synergistic activity compared to the activity of each single agent alone. Such an effect of cyclodextrin, which was up to date used only as a pharmaceutical stabilizer, was not expected.

In addition the problem is solved by providing a new class of compounds herein defined below as compounds of the structure of formula (I), and their use in the treatment of diseases. The aspect of these compounds and their medical application is disclosed herein below.

In the following a detailed description of the components of the combination of the present invention is provided. The preferred embodiments and species of each component are to be combined in any possible way with any of the preferred embodiments and species of the other components of the inventive combination.

A dithiocarbamate according to the invention has preferably the general formula: $R_1R_2NCS_2$, wherein $R_1$ and $R_2$ are the same or different, and are selected from hydrogen, and unsubstituted or substituted alkyl, unsubstituted or substituted alkenyl, unsubstituted or substituted aryl, and unsubstituted or substituted heteroaryl.

Even more preferably the dithiocarbamate is a dithiocarbamate disulfide of the formula $R_1R_2NCS_2$—$S_2CNR_3R_4$, wherein $R_1$, $R_2$, $R_3$ and $R_4$ are the same or different, and are selected from hydrogen, and unsubstituted or substituted alkyl, unsubstituted or substituted akenyl, unsubstituted or substituted aryl, and unsubstituted or substituted heteroaryl, or either $R_1$ with $R_2$ and/or $R_3$ with $R_4$ and the adjacent N atom together form an N-heterocyclic ring.

The dithiocarbamate disulfide is a disulfide form of a dithiocarbamate and for the purposes of the present invention is preferably selected from the group consisting of diethyldithiocarbamate, pyrrolidinedithiocarbamate, (N-methyl, N-ethyl)dithiocarbamates, imidazolinedithiocarbamates, dibenzyldithiocarbamate, dimethyldithiocarbamate, dipropyldithiocarbamate, dibutyldithiocarbamate, diamyldithiocarbamate, (N-methyl, N-cyclopropylmethyl) dithiocarbamate, bis(hydroxylethyl)-dithiocarbamate and N-methylglucosamine dithiocarbamate.

A preferred species of dithiocarbamate of the invention is a tetraalkyl thiuram disulfide. Most preferably the dithiocarbamate is disulfiram, which has the general formula $R_1R_2NCS_2$—$S_2CNR_3R_4$, where $R_1$, $R_2$, $R_3$ and $R_4$ are ethyl. Disulfiram is a chemical agent also known as Antabuse® or tetraethylthiuram disulfide, and is an FDA-approved drug that is widely used for the treatment of alcoholism.

According to the present invention the dithiocarbamate is combined with cyclodextrin to yield the surprising antitumor activities as shown in the appended examples. The term cyclodextrin stands here for cyclic oligosaccharides formed from glucose molecules connected via α-1,4-glycoside bonds. They comprise a Greek letter as prefix, depending on the number of glucose molecules from which they are built. α-, β-, γ- and δ-cyclodextrins with 6, 7, 8 or 9 glucose molecules are especially of importance.

The cyclodextrins according to the invention also include modified cyclodextrins. Modified cyclodextrins can in particular be obtained by modifying one or more of the primary and/or secondary hydroxyl groups. Modified cyclodextrins and methods for their synthesis are well known in art. The choice between a natural or modified cyclodextrin is less of importance according to the invention. Surprisingly, it has now been found that the addition of cyclodextrin to a dithiocarbamate for the formulation of the dithiocarbamate/heavy metal composition resulted in a product with excellent and synergistic anti-tumor activity. Thus, it is up to a person skilled in the art to use either a natural or suitably modified cyclodextrin which will result in the surprising effects of the herein disclosed invention.

A preferred cyclodextrin for use in the present invention is selected from an unsubstituted or substituted α-cyclodextrin, β-cyclodextrin, γ-cyclodextrin, hydroxypropyl-β-cyclodextrin and dihydroxypropyl-β-cyclodextrin. Most preferred is dihydroxypropyl-β-cyclodextrin, sulfobutylether-β-cyclodextrin, or methyl-β-cyclodextrin.

The cyclodextrin is most preferably selected from any of the following commercially available cyclodextrins:
alpha-cyclodextrin (CAS #: 10016-20-3)
alpha-cyclodextrin phosphate Sodium salt (CAS #: 199684-60-1)
alpha-cyclodextrin, sulfated Sodium salt Hydrate (CAS #: 699020-02-5)
Hexakis (2,3,6-tri-O-acetyl)-alpha-cyclodextrin
Hexakis (2,3,6-tri-O-methyl)-alpha-cyclodextrin
Hexakis(2,3,6-tri-O-octyl)-alpha-cyclodextrin (CAS #: 140395-31-9)
Hexakis-6-bromo-6-deoxy-alpha-cyclodextrin (CAS #: 53784-82-0)
Hexakis-6-iodo-6-deoxy-alpha-cyclodextrin (CAS #: 131105-41-4)
Hexakis (6-O-tertbutyl-dimethyl silyl)-alpha-cyclodextrin
Butyl-alpha-cyclodextrin
Succinyl-alpha-cyclodextrin
(2-Hydroxypropyl)-alpha-cyclodextrin (CAS #: 128446-33-3)
beta-cyclodextrin (CAS #: 7585-39-9)
beta-cyclodextrin Hydrate (CAS #: 68168-23-0)
beta-cyclodextrin phosphate Sodium salt (CAS #: 199684-61-2)
beta-cyclodextrin sulfate
beta-cyclodextrin, sulfated Sodium salt (CAS #: 37191-69-8)
Hydroxypropyl-beta-cyclodextrin (CAS #: 94035-02-6)
6-Monodeoxy-6-monoamino-beta-cyclodextrin
6-O-alpha-D-Glucosyl-beta-cyclodextrin (CAS #: 92517-02-7)
6-O-alpha-Maltosyl-beta-cyclodextrin Hydrate (CAS #: 104723-60-6)
Heptakis-6-azido-6-deoxy-beta-cyclodextrin Heptakis(2,3-di-O-acetyl-6-O-sulfo)-beta-cyclodextrin Heptasodium salt (CAS #: 196398-66-0)
Heptakis-(2,3-di-O-methyl-6-O-sulfo)-beta-cyclodextrin Heptasodium salt (CAS #: 201346-23-8)
Heptakis(2,6-di-O-methyl)-beta-cyclodextrin (CAS #: 51166-71-3)
Heptakis-(2,6-di-O-ethyl)-beta-cyclodextrin (CAS #: 111689-03-3)
Heptakis(2,3,6-tri-O-methyl)-beta-cyclodextrin (CAS #: 55216-11-0)
Heptakis(2,3,6-tri-O-acetyl)-beta-cyclodextrin
Heptakis-(2,3,6-tri-O-benzoyl)-beta-cyclodextrin (CAS #: 23666-43-5)
Heptakis-(2,3,6-tri-O-ethyl)-beta-cyclodextrin (CAS #: 111689-01-1)
Heptakis-6-iodo-6-deoxy-beta-cyclodextrin (CAS #: 30754-23-5)
Heptakis-6-(dimethyl-tert-butylsilyl)-6-deoxy-beta-cyclodextrin
Heptakis-6-bromo-6-deoxy-beta-cyclodextrin
Monoacetyl-beta-cyclodextrin
Diacetyl-beta-cyclodextrin
Triacetyl-beta-cyclodextrin (CAS #: 23739-88-0)
Heptakis(3-O-acetyl-2,6-di-O-methyl)-beta-cyclodextrin (CAS #: 131889-29-7)
Heptakis-(6-O-maltosyl)-beta-cyclodextrin
Heptakis(6-O-sulfo)-beta-cyclodextrin Heptasodium salt (CAS #: 197587-31-8)
Heptakis(6-O-t-butyldimethylsilyl-2,3-di-O-acetyl)-beta-cyclodextrin
Succinyl-(2-hydroxypropyl)-beta-cyclodextrin
(2,6-Di-O-)ethyl-beta-cyclodextrin
(2-Carboxyethyl)-beta-cyclodextrin
(2-Hydroxyethyl)-beta-cyclodextrin (CAS #: 128446-32-2)
(2-Hydroxypropyl)-beta-cyclodextrin (CAS #: 128446-35-5)
Butyl-beta-cyclodextrin
Methyl-beta-cyclodextrin (CAS #: 128446-36-6)
Silyl((6-O-tert-butyldimethyl)-2,3,-di-O-acetyl)-beta-cyclodextrin
Succinyl-beta-cyclodextrin
gamma-cyclodextrin (CAS #: 17465-86-0)
gamma-cyclodextrin Hydrate (CAS #: 91464-90-3)
gamma-cyclodextrin phosphate Sodium salt (CAS #: 199684-62-3)
Sulfopropyl-beta-cyclodextrin
Carboxymethyl-gamma-cyclodextrin
Octakis (2,3,6-tri-O-acetyl)-gamma-cyclodextrin
Octakis (2,3,6-tri-O-methyl)-gamma-cyclodextrin
Octakis (2,6-di-O-pentyl)-gamma-cyclodextrin
Octakis-6-(dimethyl-tert-butylsilyl)-6-deoxy-gamma-cyclodextrin
Octakis-6-bromo-6-deoxy-gamma-cyclodextrin (CAS #: 53784-84-2)
Octakis-6-iodo-6-deoxy-gamma-cyclodextrin (CAS #: 168296-33-1)
Octakis (6-O-t-butyldimethylsilyl)-gamma-cyclodextrin
Succinyl-gamma-cyclodextrin
(2-Hydroxypropyl)-gamma-cyclodextrin (CAS #: 128446-34-4)
Acetyl-gamma-cyclodextrin
Butyl-gamma-cyclodextrin
Betadex Sulfobutyl Ether One of the particularly preferred cyclodextrins of the invention is hydroxypropyl-beta-cyclodextrin (CAS #: 94035-02-6) or methyl-beta-cyclodextrin (CAS #: 128446-36-6) or SBE-β-CD|Sulfobutylether-β-cyclodextrin (CAS #: 182410-00-0).

The "heavy metal source" or "heavy metal ion source" shall refer to any compound providing the heavy metal atom for the formation of a complex of the heavy metal and the dithiocarbamate of the invention. Particularly preferred heavy metals are selected from arsenic, bismuth, cobalt, copper, chromium, gallium, gold, iron, manganese, nickel, platin, silver, titanium, vanadium, selenium, and zinc; and preferably the source is a copper or more preferably gold source.

In some embodiments the heavy metal ion source is a chelate of a heavy metal ion and a sulfate salt, a chloride salt or an organic anion, such as acetate, dithiocarbamate, lactate, glycinate, citrate, propionate, and gluconate. As mentioned already above, in some embodiments the source of the heavy metal according to the invention is a dithiocarbamate-metal complex. In this embodiment in particular complexes of gold and copper with disulfiram is preferred. Metal complexes of dithiocarbamates are known for example from Hogarth G.: "Metal-dithiocarbamate complexes: chemistry and biological activity." (Mini Rev Med Chem. 2012 October; 12(12):1202-15. Review. PubMed PMID: 22931592; incorporated by reference in its entirety), in particular the structures of FIG. 9. A preferred complex has the following structure I:

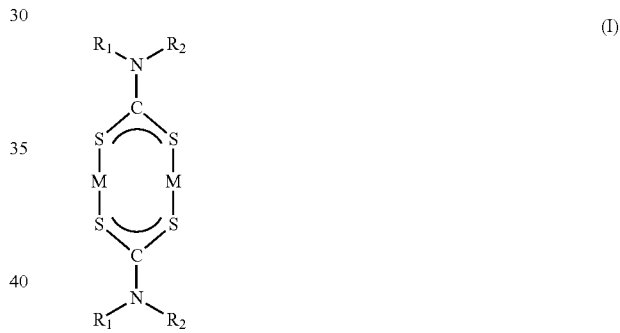

Wherein $R_1$ and $R_2$ are the same or different, and are selected from hydrogen, and unsubstituted or substituted alkyl, unsubstituted or substituted akenyl, unsubstituted or substituted aryl, unsubstituted or substituted alkoxy, and unsubstituted or substituted heteroaryl; and preferably are ethyl; and wherein M is a metal ion.

In some preferred embodiments the compounds of the invention (the complexes) are in polymeric form—so-called catena-complexes—due to linear metal-metal interactions.

In some aspects the present invention further pertains to the following complexes of formula (I), wherein the $R_1$ and $R_2$ are the same or different, and are selected from hydrogen, and unsubstituted or substituted $C_1$ to $C_{10}$, preferably $C_1$ to $C_5$ alkyl, unsubstituted or substituted $C_1$ to $C_{10}$, preferably $C_1$ to $C_5$ akenyl, unsubstituted or substituted aryl, unsubstituted or substituted alkoxy, and unsubstituted or substituted heteroaryl; and preferably are ethyl; and wherein M is a metal ion selected from Au or Cu.

An alkyl or alkenyl may be straight, branched or cyclic in context of the invention.

The term "substituted", as used herein, in relation to the above moieties refers to a substituent other than hydrogen. Such a substituent is preferably selected from the group consisting of halogen, —$CF_3$, —$C_2F_5$, —$C_3F_7$, —$C_4F_9$, —C$_5$F$_{11}$, and other fluoroalkyl of 2 to 5 carbons, —OH, —NH$_2$, —NO$_2$, —CHO, —CN, —COOH, —SH, —SO$_2$OH, —CONH$_2$, —NHNH$_2$, —OR, —NRR', —C(O)R, —C(O)OR, (CO)NRR', —NR'C(O)R, —OC(O)R, aryl with 5 to 10 carbon atoms, cycloalk(en)yl with 3 to 20 carbon atoms, 3- to 8-membered heterocycloalk(en)yl, and 5- to 10-membered heteroaryl, wherein R and R' are independently selected from hydrogen, alkyl with 1 to 10 carbon atoms, alkenyl with 2 to 10 carbon atoms, alkynyl with 2 to 10 carbon atoms, aryl with 5 to 14 carbon atoms, cycloalk(en)yl with 3 to 20 carbon atoms, 5- to 14-membered heteroaryl, comprising 1 to 4 heteroatoms selected from nitrogen, oxygen, and sulfur, and 5- to 14-membered heterocycloalk(en)yl, comprising 1 to 4 heteroatoms selected from nitrogen, oxygen, and sulfur. In some embodiments any of these substituents may again be substituted, it is however preferred that these substituents are unsubstituted.

In some embodiments R$_1$ and R$_2$ may be connected to form a 4, 5, 6, 7 or 8-membered N-heterocyclic ring system, which is optionally substituted.

The term "alkyl", as used herein, refers to a saturated hydrocarbon moiety, such as methyl, ethyl, and the like. The terms "alkenyl" and "alkynyl", as used herein, comprise aliphatic residues with at least one carbon-carbon double bond or triple bond, respectively, and are otherwise defined as "alkyl".

The term "cycloalkyl", as used herein, refers to a non-aromatic carbocyclic moiety, such as cyclopentanyl, cyclohexanyl, and the like. The term "cycloalkenyl", as used herein, refers to non-aromatic carbocyclic compounds that comprise at least one carbon-carbon double bond.

Similarly, the term "heterocycloalk(en)yl" as used herein, relates to cycloalk(en)yl groups wherein 1 or more ring carbon atoms are replaced by heteroatoms, preferably selected from nitrogen, oxygen, and sulfur.

The term "aryl", as used herein, relates to an aromatic ring that is preferably monocyclic or consists of condensed aromatic rings. Preferred aryl substituents are moieties with 6 to 14 carbon atoms, such as phenyl, naphthyl, anthracenyl, and phenanthrenyl.

The term "heteroaryl" as used herein, refers to aromatic moieties that correspond to the respective aryl moiety wherein one or more ring carbon atoms have been replaced by heteroatoms, such as nitrogen, sulfur, oxygen, phosphorus. Preferred heteroaryls are pyrrolyl, imidazolyl, furanyl and thiophenyl and the like.

As used herein, the term "metal ion" refers to elements of the periodic table that are metallic and that are negatively or positively charged as a result of having more or fewer electrons in the valence shell than is present for the neutral metallic element. Metals that are useful in the present invention include the earth metals, alkali earth metals, transition metals and post-transition metals. Alkali metals include Li, Na, K, Rb and Cs. Alkaline earth metals include Be, Mg, Ca, Sr and Ba. Transition metals include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Post-transition metals include Al, Ga, In, Tl, Ge, Sn, Pb, Sb, Bi, and Po. One of skill in the art will appreciate that the metals described above can each adopt several different oxidation states, all of which are useful in the present invention. Preferred metals are Au and Cu.

Preferred complexes according to the invention have any one of the following structures:

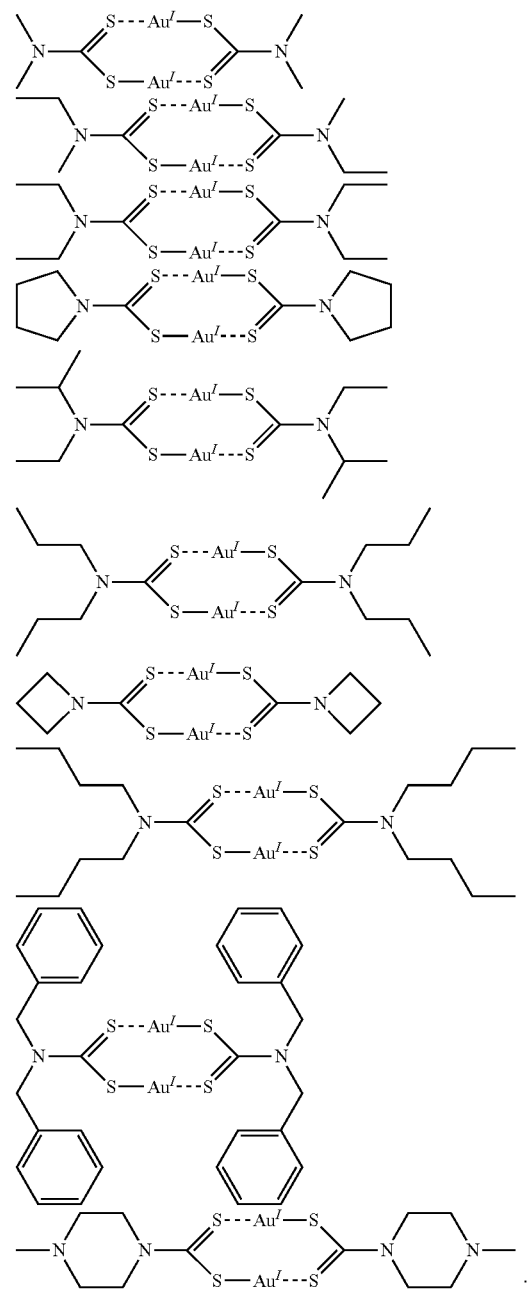

In another aspect of the present invention there is provided the use of a complex according to the above structure (I) in the treatment of a disease as disclosed herein elsewhere.

A compound for use in a treatment is preferred, wherein the treatment comprises administration of the compound together with a cyclodextrin, preferably wherein the compound is administered as a pharmaceutical composition comprising the compound together with a cyclodextrin. The cyclodextrin is preferably selected as stated elsewhere herein.

Another aspect then pertains also to a pharmaceutical composition for use in the treatment of a disease, comprising a compound or complex as disclosed herein, together with a cyclodextrin and a pharmaceutical acceptable carrier and/or excipient.

In another aspect the invention provides any one the following compounds:

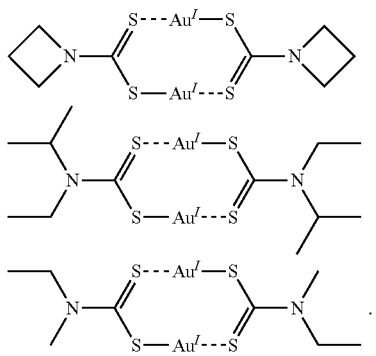

Compounds of the herein disclosed invention are particularly useful in the treatment of tumor diseases which are resistant to other chemotherapeutic agents (chemotherapy resistant tumor diseases). Such tumor resistance may occur after a treatment with a prior art chemotherapeutic. In the herein provided examples, the inventors could show that chemotherapy resistance to etoposide or cisplatin could be overcome by subsequent treatment with the compounds of the invention.

The term "chemotherapy-resistant tumor" as used herein refers to a tumor disease, including the individual cells therein, that is or becomes refractory to treatment by a chemotherapy, such as the therapy with a chemotherapeutic agent, for example etoposide or platin compounds. In specific embodiments, the chemotherapy-resistant tumor becomes resistant after initiation of the treatment and may occur during the treatment. In further specific embodiments, the resistance to chemotherapy manifests at about 2-24 months while the patient is receiving chemotherapy. In de novo resistance, the patient does not respond to initial therapy. Acquired resistance is where the patient develops metastatic disease during therapy. Acquired resistance to chemotherapy is well-known in the art. In particular, small cell lung cancer patients while undergoing treatment with chemotherapy have recurrence of the disease, usually resulting in the death of the patient. In specific embodiments, the disease metastasizes during therapy with anthracycline based chemotherapy, which results in resistant metastases.

Preferred metal sources of the invention may be selected from auranofin, aurothiomalate, Au-dithiocarbamate, aurothioglucose, copperchloride and coppersulfate.

According to the invention a preferred combination pertains to the combination of a disulfiram, a copper or gold complex, and a cyclodextrin as described herein above.

In a preferred embodiment of the invention a combination is preferred wherein the dithiocarbamate, the source of a heavy metal and the cyclodextrin are in admixture in the combination and not spatially separated.

In some embodiments it might be preferred that the combination of the invention further comprises at least one additional cytotoxic compound. In cancer therapy it is often useful to combine cancer therapeutics with different modes of anti-cancer activity to avoid the development of resistant forms of the disease. The at least one additional cytotoxic compound may be selected from cyclophosphamide ifosfamide, hexamethylmelamine, tirapazimine, sertenef, cachectin, tasonermin, lonidamine, carboplatin, mitomycin, altretamine, prednimustine, dibromodulcitol, ranimustine, fotemustine, nedaplatin, oxaliplatin, temozolomide, doxorubicin heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine) platinum, benzylguanine, glufosfamide, GPX100, diarizidinylspermine, arsenic trioxide, zorubicin, idarubicin, daunorubicin, bisantrene, mitoxantrone, pirarubicin, pinafide, valrubicin, amrubicin, antineoplaston, annamycin, galarubicin, elinafide, MEN10755, and 4-demethoxy-3'-deamino-3'-aziridinyl-4-methylsulphonyldaunorubicin, rapamycin and its derivatives, sirolimus, temsirolimus, everolimus, zotarolimus and deforolimus. Also included in the definition are microtubulin inhibitors include paclitaxel, vindesine sulfate, 3',4'-didehydro-4'-deoxy-8'-norvincaleukoblastine, docetaxel, rhizoxin, dolastatin, mivobulin isethionate, auristatin, cemadotin, RPR109881, BMS 184476, vinflunine, cryptophycin, 2,3,4,5,6-pentafluoro-N-(-3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, BMS 188797, topotecan, hycaptamine, irinotecan, rubitecan, 7-[2-(N-isopropyl amino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, 6,9-bis[(2-amino-ethyl)amino]benzo[g]isoquinoline-5,10-dione, N-[1-[2(diethylamino)ethylamino]-7-methoxy-9-oxo-9H-thioxanthen-4-ylmethyl]formamide, N-(2-(dimethylamino)ethyl)acridine-4-carboxamide, and dimesna.

Preferred for the combination with disulfiram are in particular carboplatin, oxaliplatin, cisplatin and/or etoposide, vinorelbine, or similar compounds.

In preferred embodiments of the invention the combination comprises cyclodextrin in amounts higher than the amount of the dithiocarbamate, or dithiocarbamate/metal complex respectively. Therefore, the invention pertains to inventive combination wherein the (molar) ratio of cyclodextrin:dithiocarbamate, or cyclodextrin:dithiocarbamate/metal, ranges from at least 0.1 (1:10) to 500 (500:1). More preferred are ratios of 2, 5, 10, 50, 100, and most preferred is a ratio of about 500+/−50, or even higher.

The combination of the invention may include the components in the form of a kit, either in separate or admixed form. The components in the kit could be provided in liquid form or in solid form, for example to allow for a resuspension or solution of the components in a pharmaceutically acceptable liquid right before use. The kit of the invention may in some embodiments comprise the source of the heavy metal separately from the dithiocarbamate (not admixed with the dithiocarbamate).

The components of the combination may be combined or are separate pharmaceutical composition(s), and wherein the pharmaceutical composition(s) of the single or multiple components further comprise(s) a pharmaceutically acceptable carrier and/or excipient. A pharmaceutical composition comprising the combination of the invention is a preferred embodiment of the invention.

A pharmaceutical composition of the invention may be in the form of solid components, a lyophilized solution, an injectable solution, or a solid composition (lyophilized composition of the single or combined components of the combination of the invention) for the preparation of an injectable solution, a capsule, a tablet, a cream, an ointment, or an oral or nasal inhalation composition.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The combination, or compounds, according to the invention is for use in medicine, and preferably for the treatment of a proliferative disease such as a tumor disease, infectious diseases, cardiovascular disorders, rheumatic arthritis, or persisting HIV infection.

The compounds of the present invention are useful in the preparation of medicaments to treat any of the above disorders. The methods and techniques for preparing medicaments of a compound of the invention are well-known in the art. Exemplary pharmaceutical formulations and routes of delivery are described herein elsewhere.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

Most preferably the disease to be treated according to the invention is cancer. A cancer according to the invention may be selected from a solid or liquid tumor disease, preferably selected from fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, anal carcinoma, esophageal cancer, gastric cancer, hepatocellular cancer, bladder cancer, endometrial cancer, pancreatic cancer, brain cancer, breast cancer, ovarian cancer, prostate cancer, stomach cancer, atrial myxomas, squamous cell carcinoma, basal cell carcinoma, adenocarcinoma, sweat gland carcinoma, sebaceous gland carcinoma, thyroid and parathyroid neoplasms, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small-cell lung cancer, bladder carcinoma, epithelial carcinoma, glioma, pituitary neoplasms, astrocytoma, medulloblastoma, craniopharyngioma, ependymoma, pinealoma, hemangioblastoma, acoustic neuroma, schwannomas, oligodendroglioma, meningioma, spinal cord tumors, melanoma, neuroblastoma, pheochromocytoma, Types 1-3 endocrine neoplasia, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

A preferred group of tumor diseases to be treated with the combinations, compounds and compositions of the invention is selected from lung cancer, colon carcinoma, ovary cancer, liver cancer, mamma carcinoma, pancreatic cancer, melanoma, glioma, T-cell lymphoma, leukemia, and Burkitt lymphoma.

In two particular preferred embodiments the cancer to be treated or prevented in context of the herein disclosed invention is SCLC (most preferred) or alternatively lymphoma. As supported by the appended examples, the compounds and compositions of the invention are surprisingly effective in the treatment of SCLC for which effective treatment strategies are desperately needed. Also lymphoma was surprisingly well treatable with the compounds and compositions of the invention.

A preferred embodiment of the invention pertains to the use of the combination or compounds for use in the treatment of a chemotherapy resistant tumor disease, for example a tumor disease characterized by the expression of an ABC transporter protein such as MDR1. The surprising synergism between the dithiocarbamate/metal complex and cyclodextrin allows overcoming chemotherapy resistance in tumor disorders and therefore provides new therapeutic strategies for patients in advanced disease stages. Therefore, the tumor disease is in some embodiments a refractory tumor disease.

Although many routes for administration of the combination or compounds of the invention are included by this invention, a preferred embodiment relates to formulations of the combinations of the invention which are suitable for parenteral administration. Such formulations include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

Various delivery systems are known and can be used to administer a therapeutic agent (e.g., a combination of disulfiram/metal ion and cyclodextrin according to the invention), e.g., encapsulation in liposomes, micro particles, microcapsules, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

The combination and compounds of the invention for the purposes of treatment can be administered to subjects or individuals diagnosed with for example a cancer disease. When the agent is administered to a subject such as a mouse, a rat or a human patient, the agent can be added to a pharmaceutically acceptable carrier and systemically or topically administered to the subject.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 500 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient. Desirable blood levels of the agent may be maintained by a continuous infusion to provide a therapeutic amount of the active ingredient within disease tissue. The use of operative combinations is contemplated to provide therapeutic combinations requiring a lower total dosage of each component than may be required when each individual therapeutic compound or drug is used alone, thereby reducing adverse effects.

The compounds of the invention or components of the combination are administered either to the subject separately, or one component separately, and the other two combined, or all combined. For example in some embodiment it might be preferred that the source of a metal ion is administered to the subject separately from the dithiocarbamate. In other embodiments the dithiocarbamate and the cyclodextrin are administered as one composition simultaneously.

Another aspect of the invention then pertains to a method for the preparation of a dithiocarbamate-containing pharmaceutical composition, comprising the step of admixing the dithiocarbamate with a cyclodextrin. In this aspect all compounds of the compositions are as defined herein above. The admixing of the dithiocarbamate with a cyclodextrin is preferably done prior to the addition of a source of metal.

Yet a further aspect of the invention then provides a method for inhibiting or reducing complex formation between a dithiocarbamate and a metal ion, the method comprising the step of admixing the dithiocarbamate and the metal ion in the presence of a cyclodextrin. Preferably the dithiocarbamate is admixed first with the cyclodextrin, and then subsequently the source of the heavy metal is added to the mixture.

In another aspect the invention relates to a method for producing a complex of structure I:

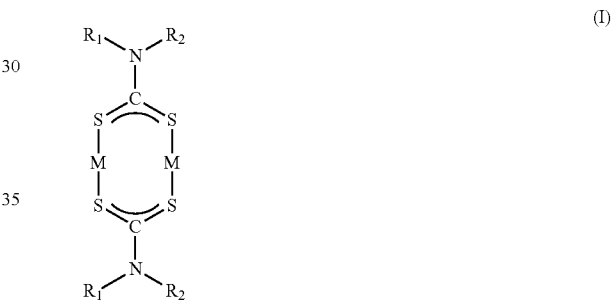

Wherein $R_1$ and $R_2$ are the same or different, and are selected from hydrogen, and unsubstituted or substituted alkyl, unsubstituted or substituted akenyl, unsubstituted or substituted aryl, and unsubstituted or substituted heteroaryl; and preferably are ethyl, M is a metal ion;

the method comprising the steps of reacting dithiocarbamate with a source of a heavy metal ion in the presence of cyclodextrin. Preferably, the dithiocarbamate is admixed first with the cyclodextrin, and subsequently the metal ion is added to the mixture.

The present invention will now be further described in the following examples with reference to the accompanying figures and sequences, nevertheless, without being limited thereto. For the purposes of the present invention, all references as cited herein are incorporated by reference in their entireties. In the example section either a "," or "." is used as decimal mark. In the Figures:

FIG. 1: The effect of cyclodextrin formulation of disulfiram on the anti-tumor potency of metals.

Figure 2:
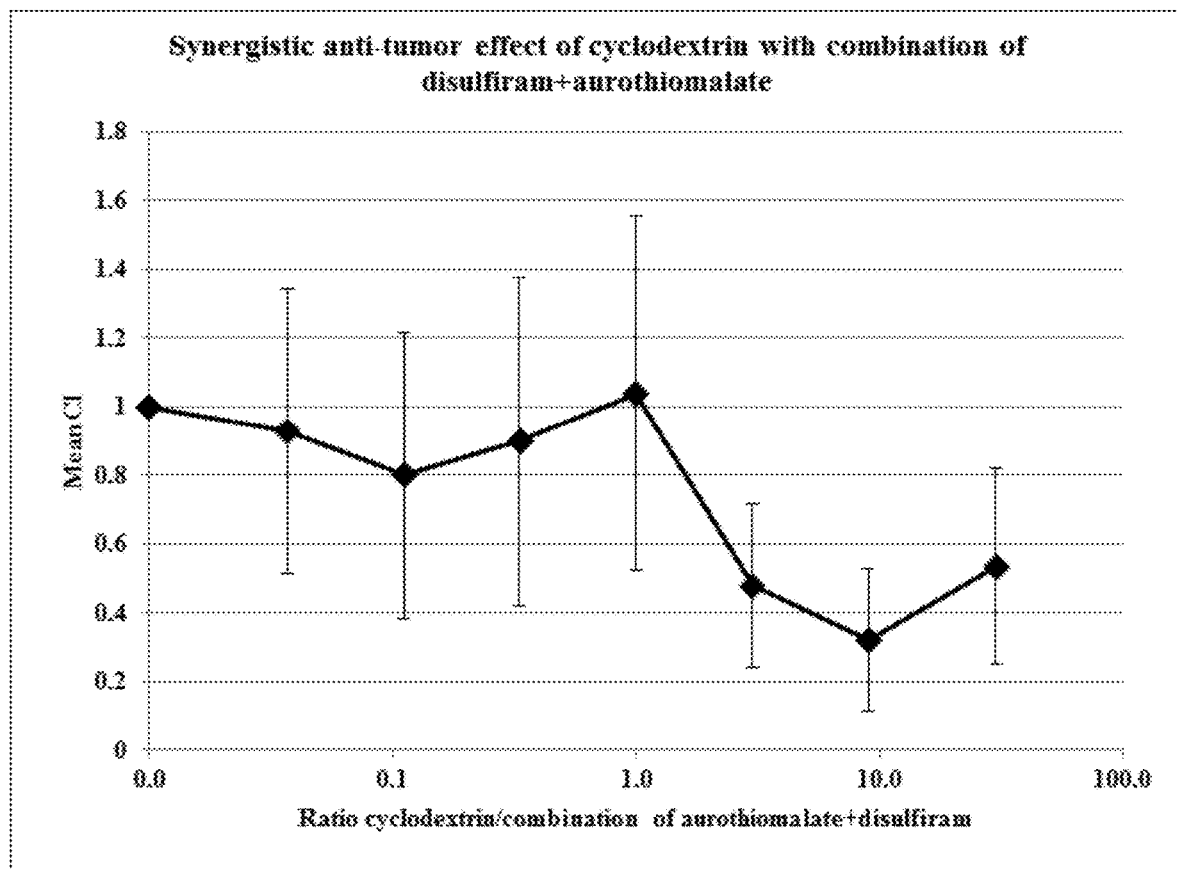

FIG. 2: Synergistic anti-tumor effect of aurothiomalate/disulfiram with cyclodextrin.

Figure 3:
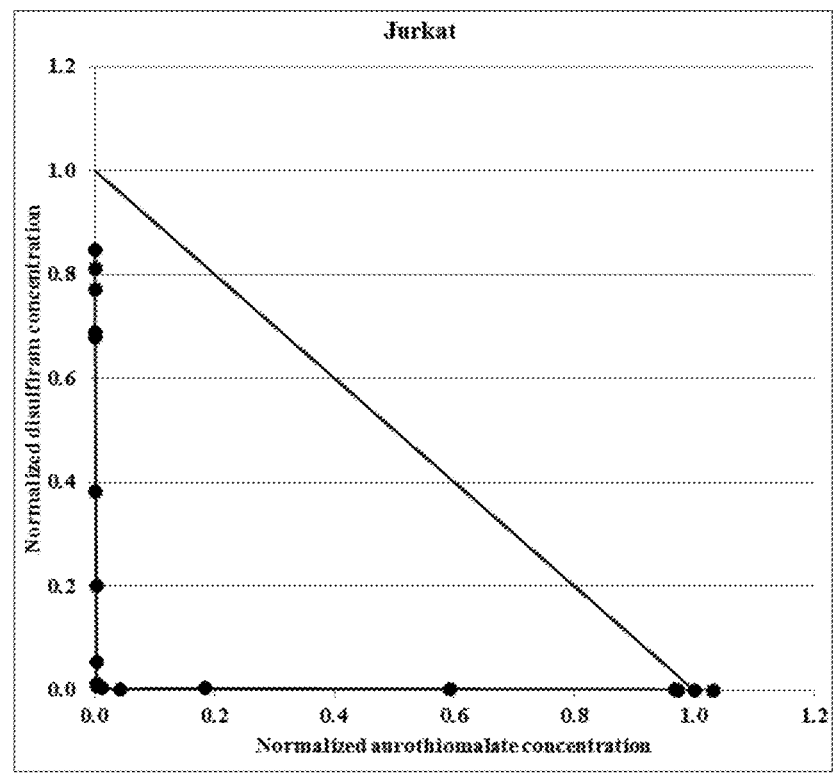
Figure 3:
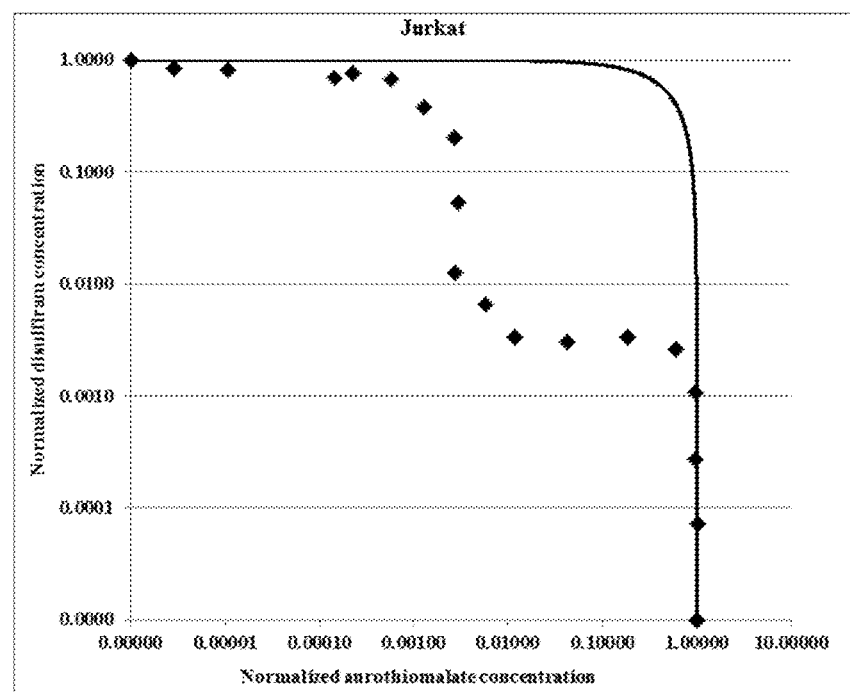
Figure 3:
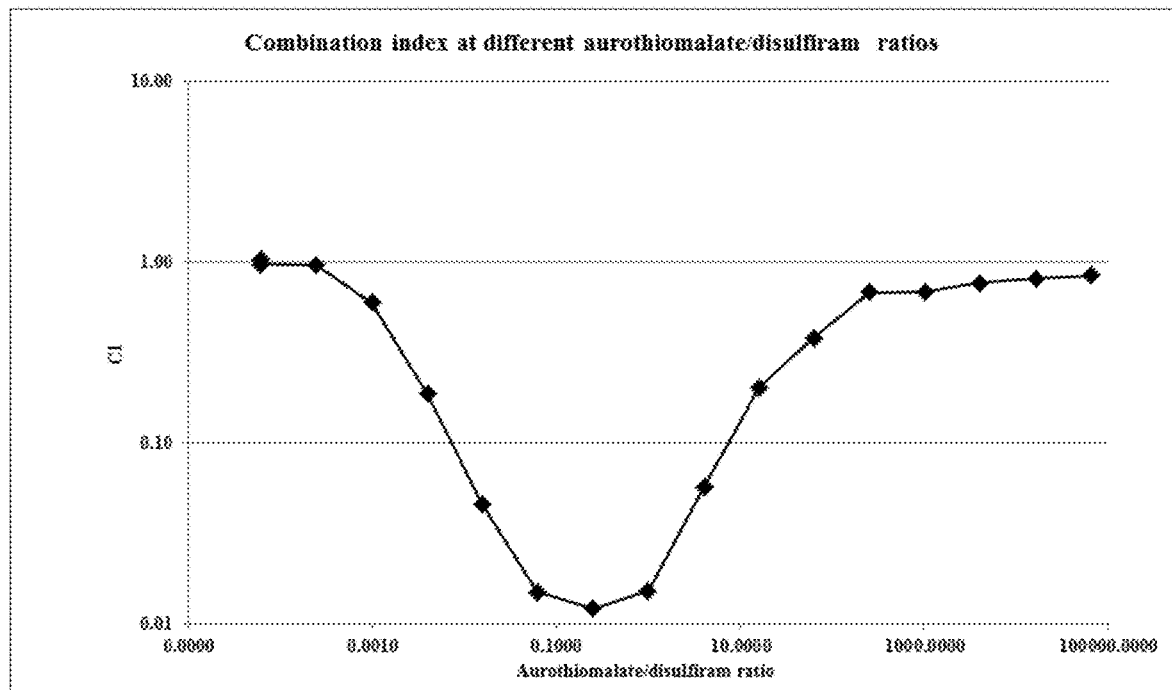

FIG. 3: A: Normalized IC50ies were plotted in an isobologram; B: IC50ies of disulfiram were plotted against IC50ies of aurothiomalate in a logarithmic scale; C: Combination index (CI)) was plotted against the ratio of aurothiomalate/disulfiram.

Figure 4:
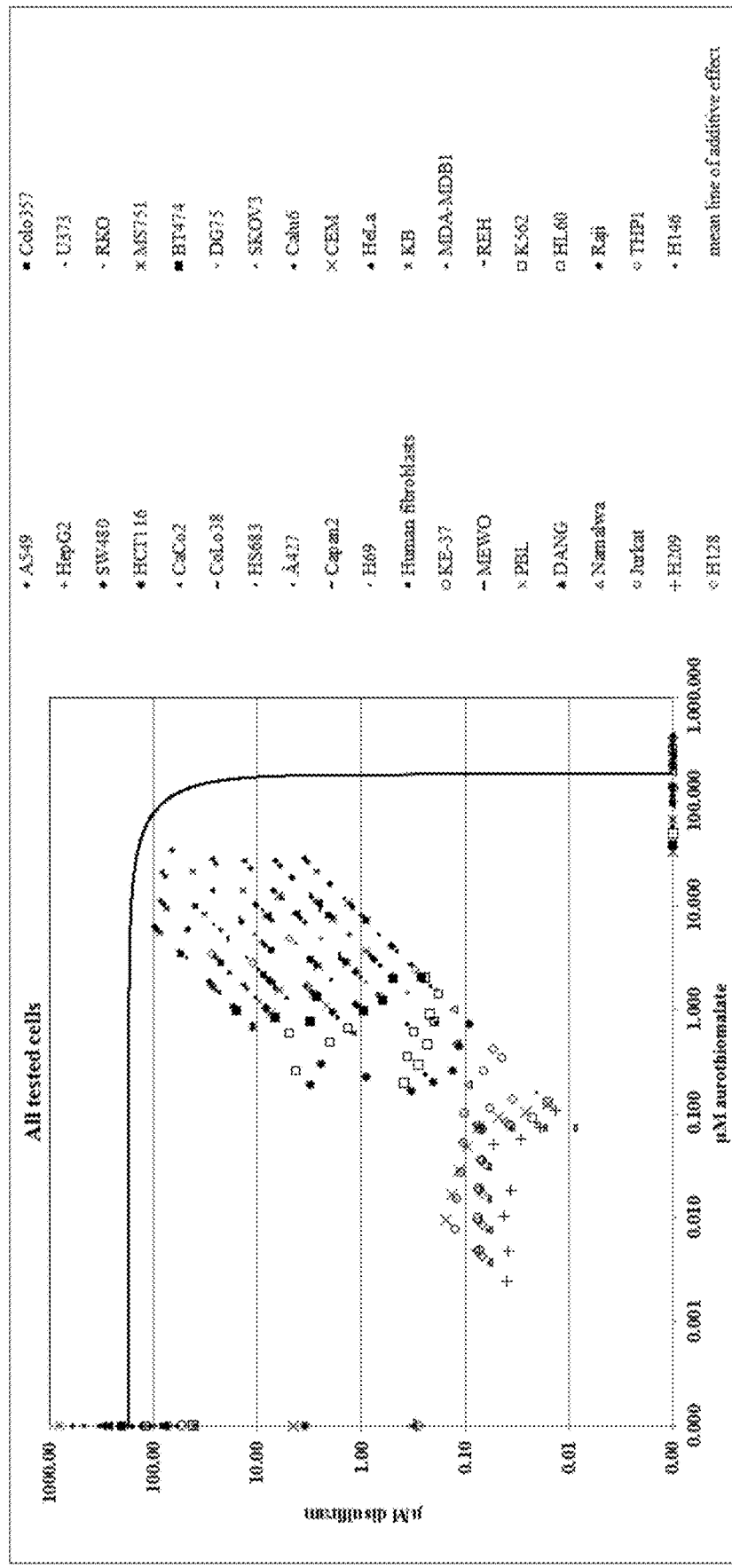
Figure 4:
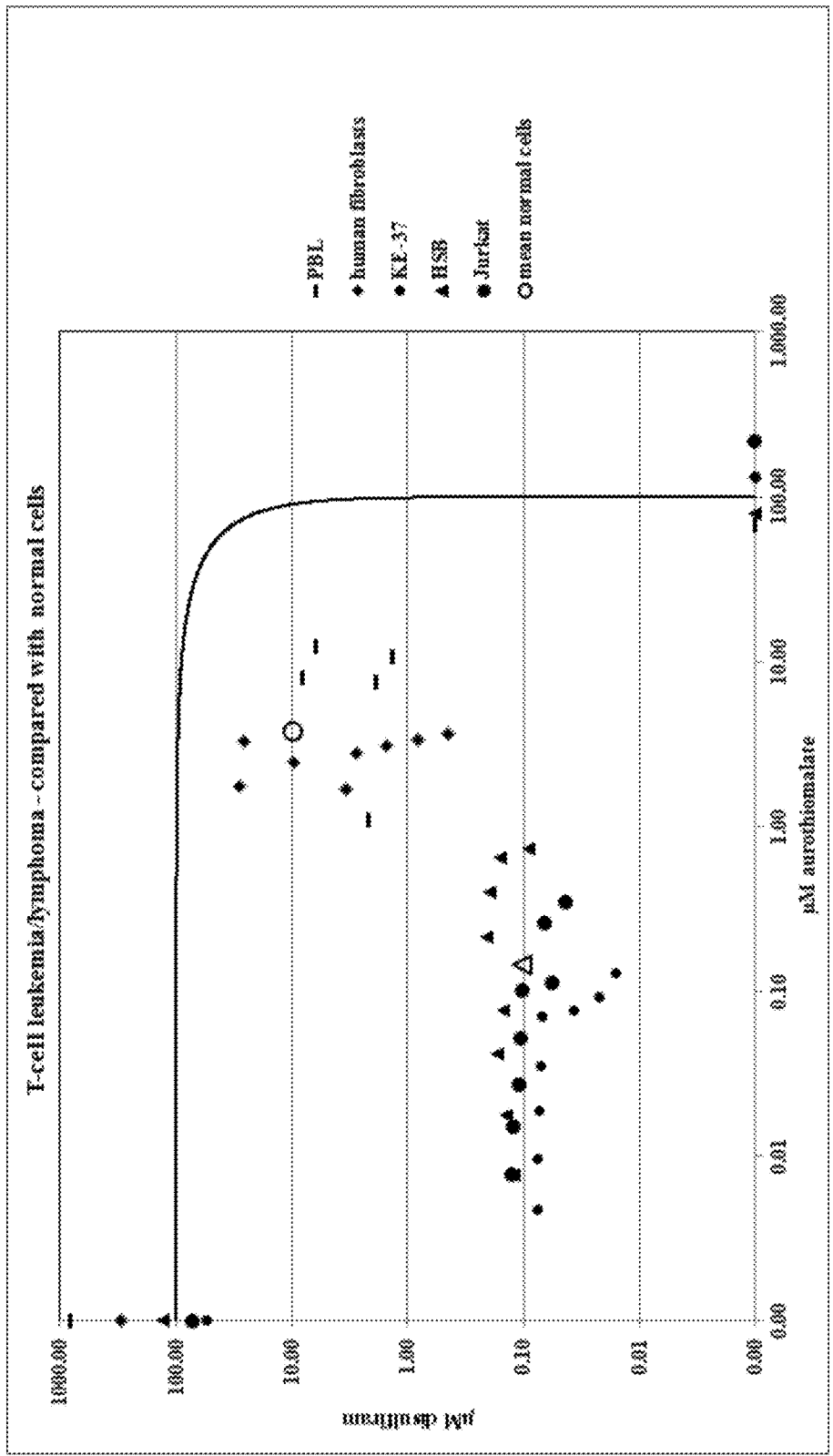
Figure 4:
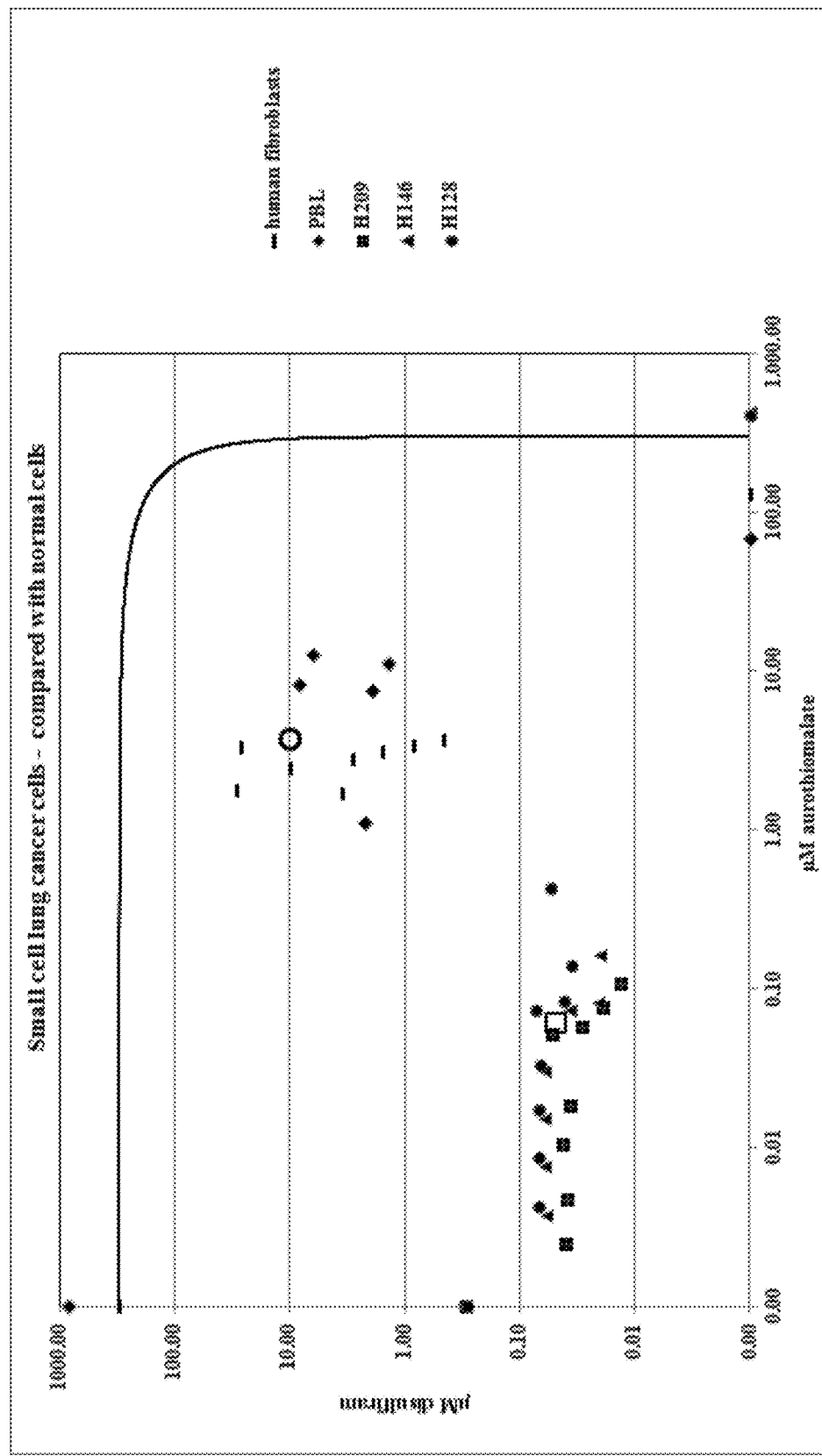
Figure 4:
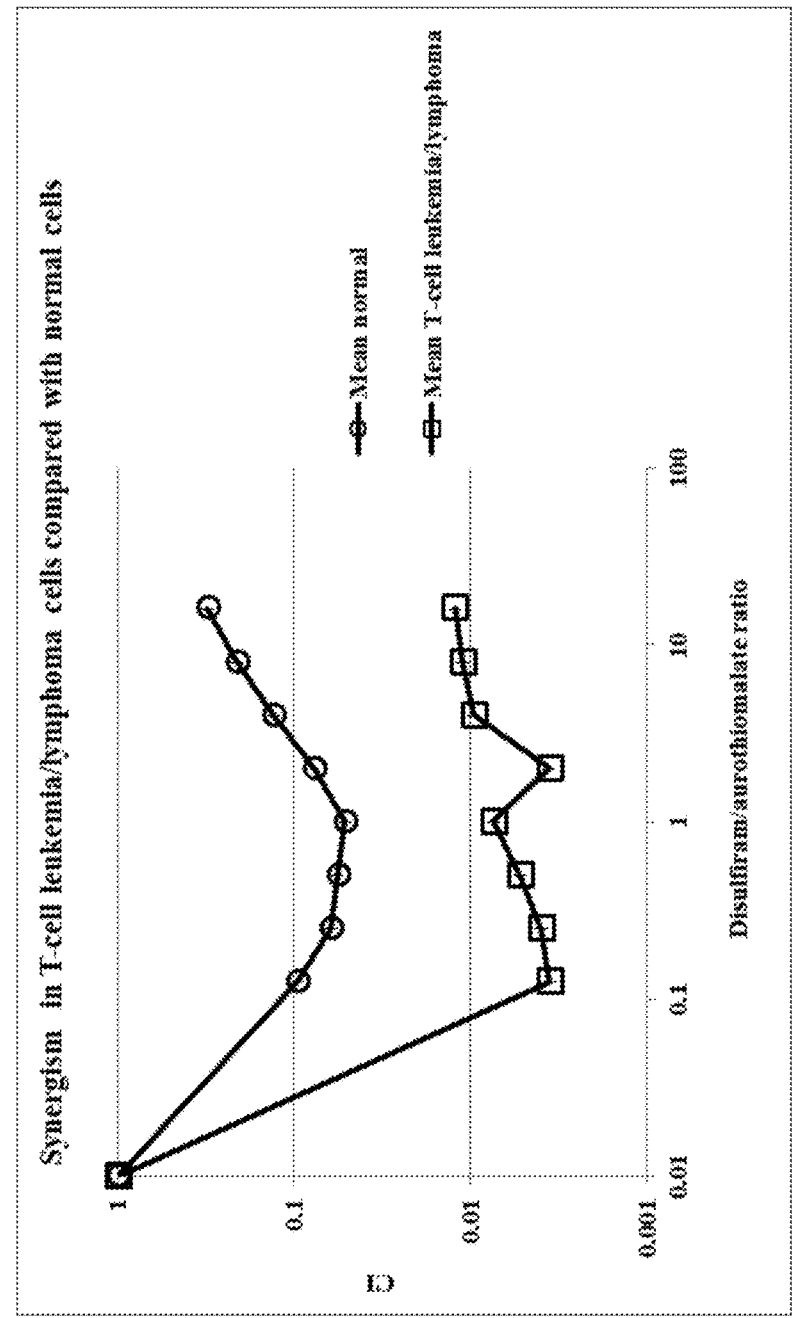

FIG. 4: A: Spectrum of anti-tumor activity of aurothiomalate/disulfiram in cyclodextrin formulation: The IC50 concentration of aurothiomalate was plotted against the corresponding concentration of disulfiram in log scale for each tested cell for each tested aurothiomalate/disulfiram ratio. Curved line indicates zone of additivity effects, calculated from the mean of IC50ies of single treatments from all tested cells. B: Selectivity of aurothiomalate/disulfiram in cyclodextrin formulation for T-cell leukemia/lymphoma cells. IC50ies of T-cell Leukemia/lymphoma compared to normal human PBL and normal human fibroblast cells; C: Selectivity of aurothiomalate/disulfiram in cyclodextrin formulation for SCLC lines. IC50ies of SCLC compared to normal human PBL and normal human fibroblast cells D: Comparison of Combination Index of aurothiomalate/disulfiram at various ratios in T-cell Leukemia/lymphoma and normal human cells (PBLs and skin fibroblasts). Normalized IC50: IC50ies were normalized to the IC50ies of single drugs by dividing IC50 of either aurothiomalate or disulfiram through IC50 of each individual drug combination. CI=Normalized IC50 of aurothiomalate concentration+normalized IC50 disulfiram concentration. Mean CI: Mean values+/−standard deviation were calculated from CIs of either all T-cell leukemias or all normal cells.

Figure 5:
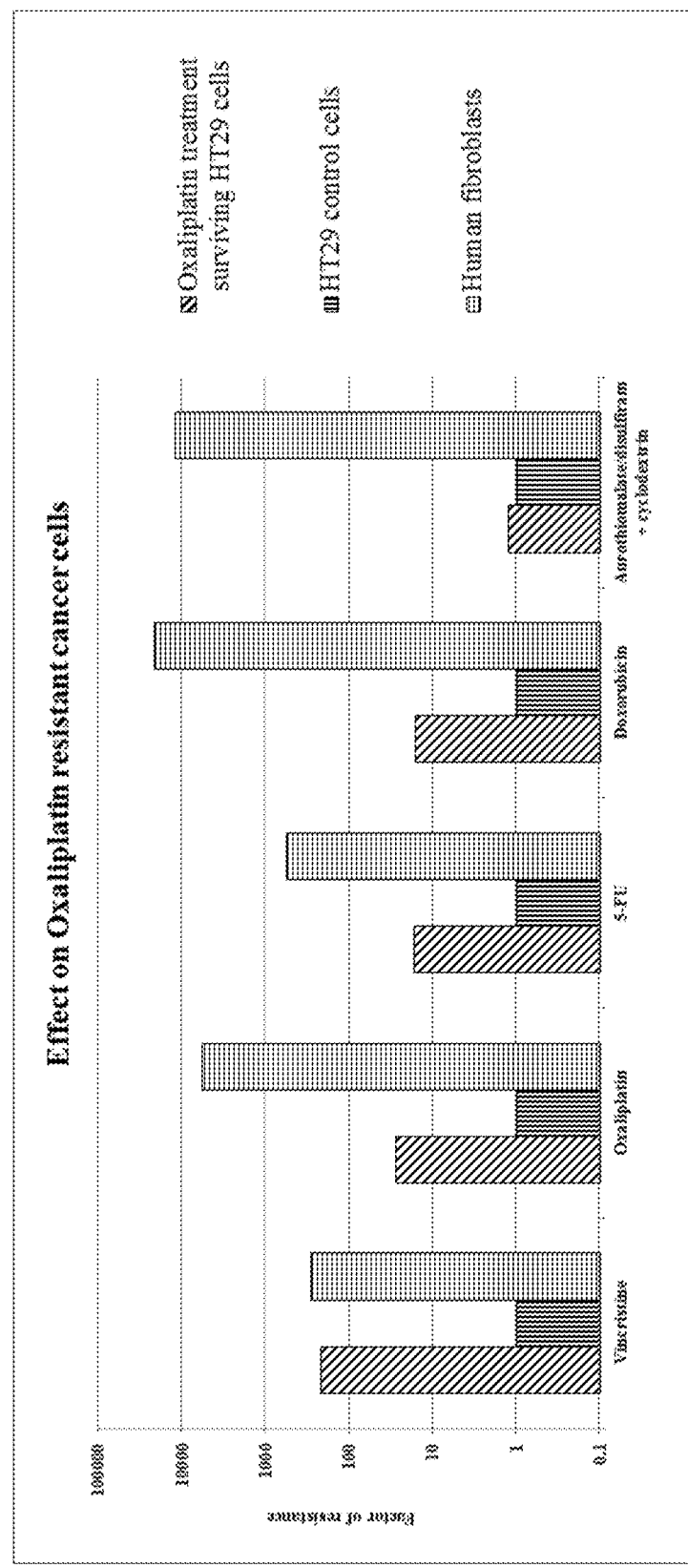

FIG. 5: Factor of resistance (IC50 of Oxaliplatin treatment surviving HT29 cells/IC50 of naive HT29 cells or normal human fibroblasts) for Vincristin, Oxaliplatin, 5-FU, Doxorubicin and aurothiomalate/disulfiram in cyclodextrin.

Figure 6:
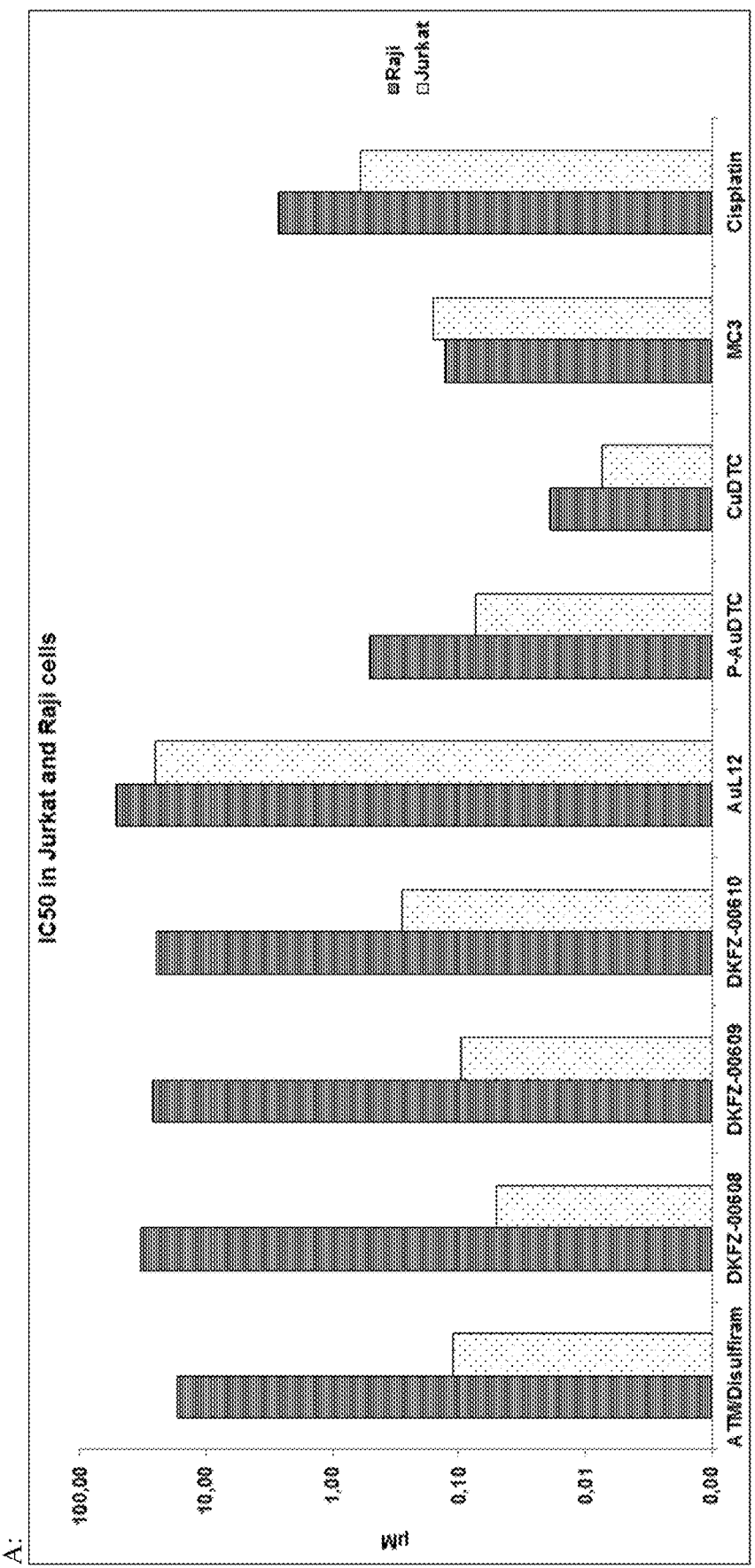
Figure 6:
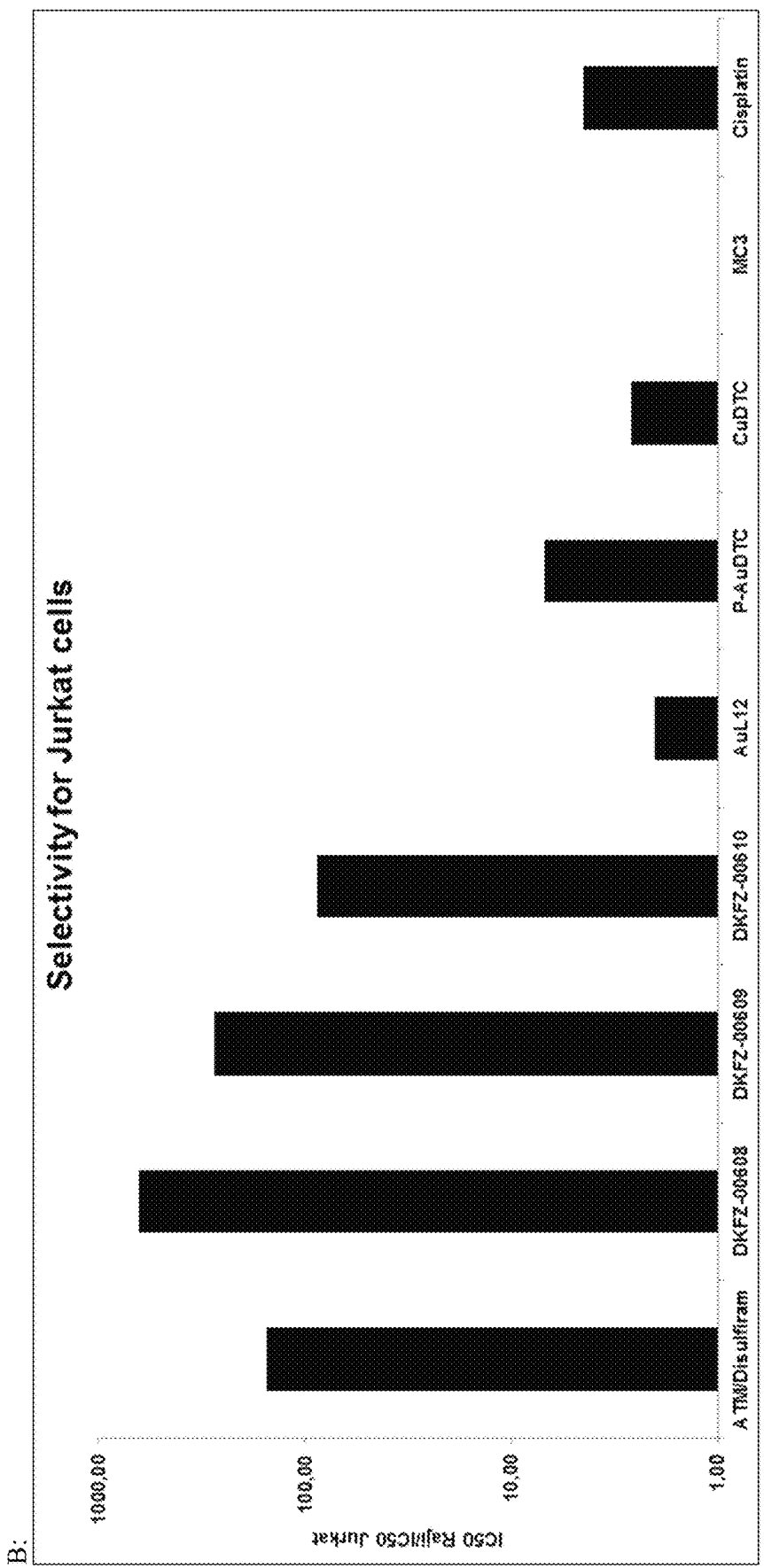

FIG. 6: A: shows IC50 values for tested compounds in Raji and Jurkat cell lines. B: shows the selectivity factor of compounds tested.

Figure 7:
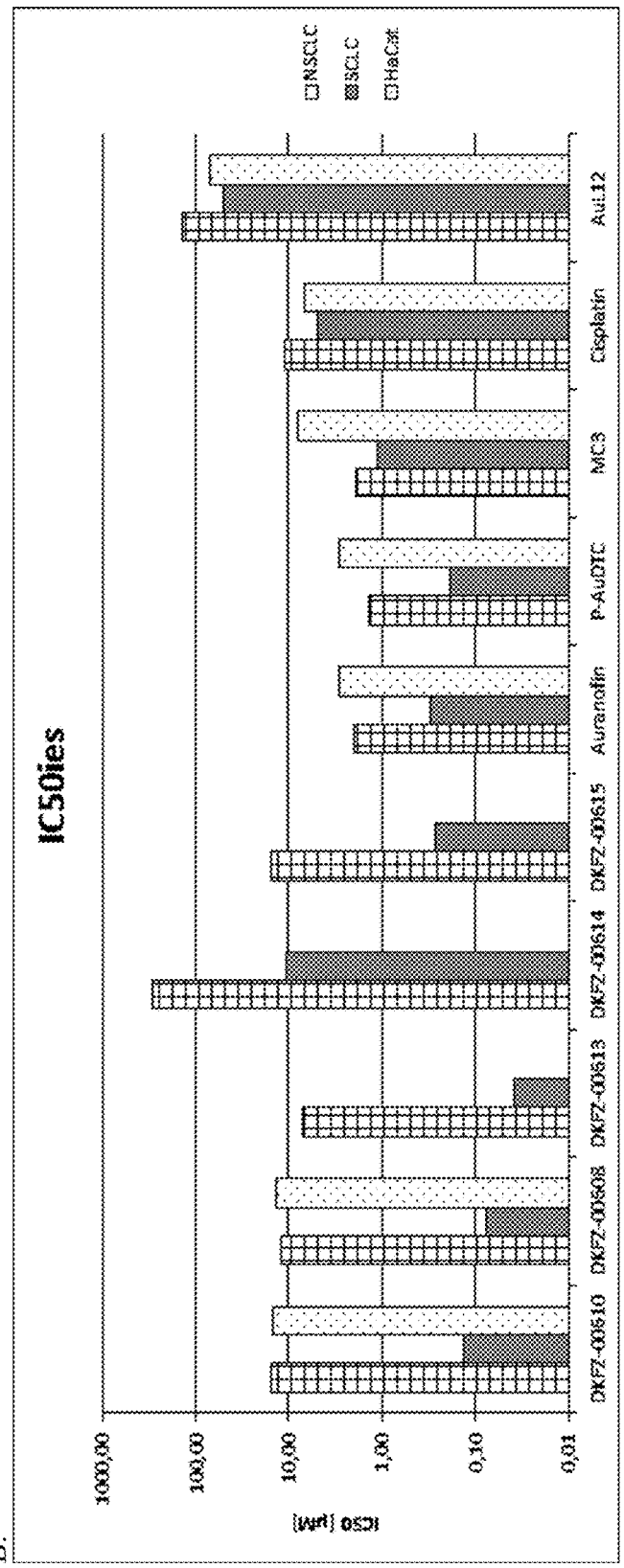
Figure 7:
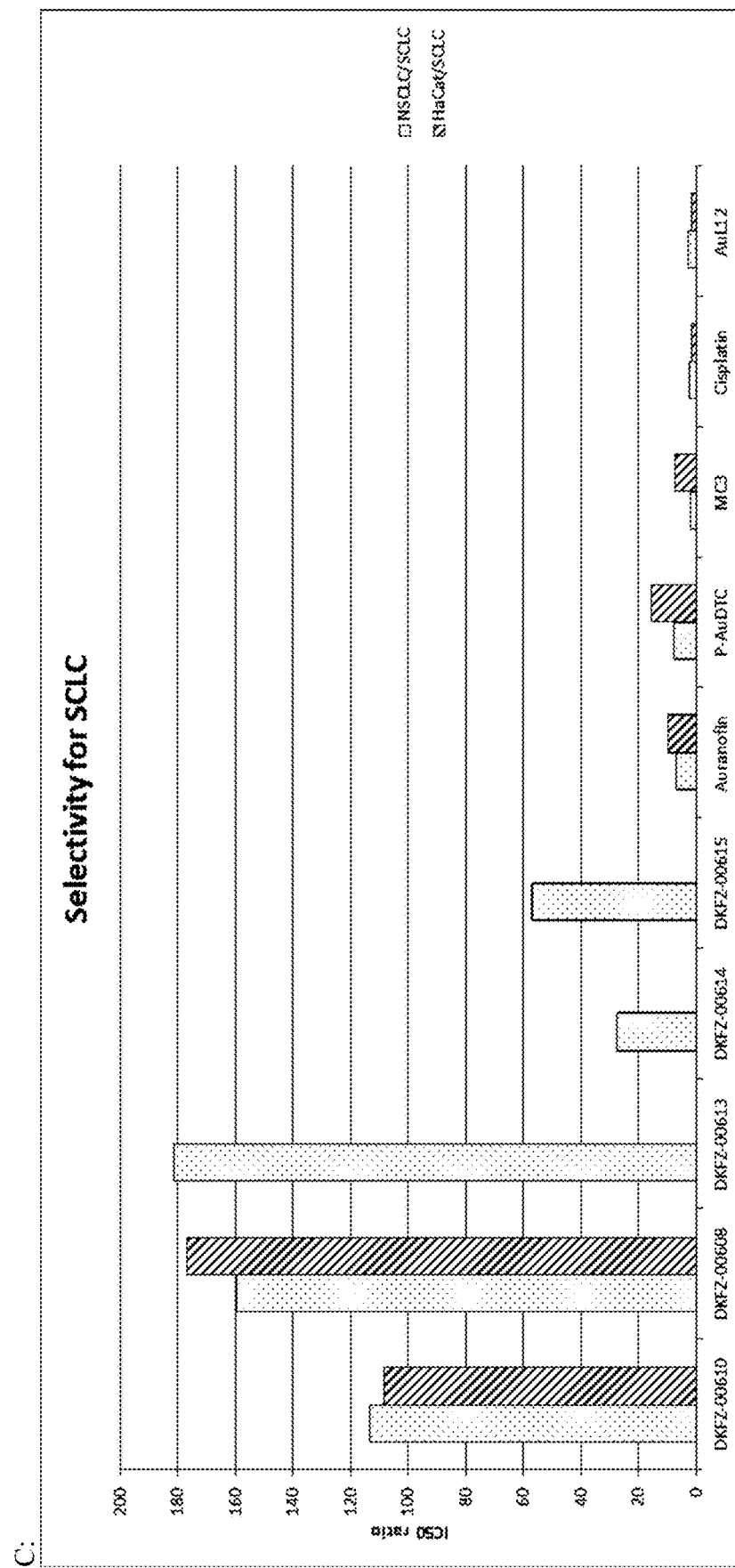

FIG. 7: shows IC50 values of tested compounds in various SCLC, NSCLC and HaCat cells. Also shown is the selectivity of tested compounds for SCLC.

Figure 8:
Figure 8:
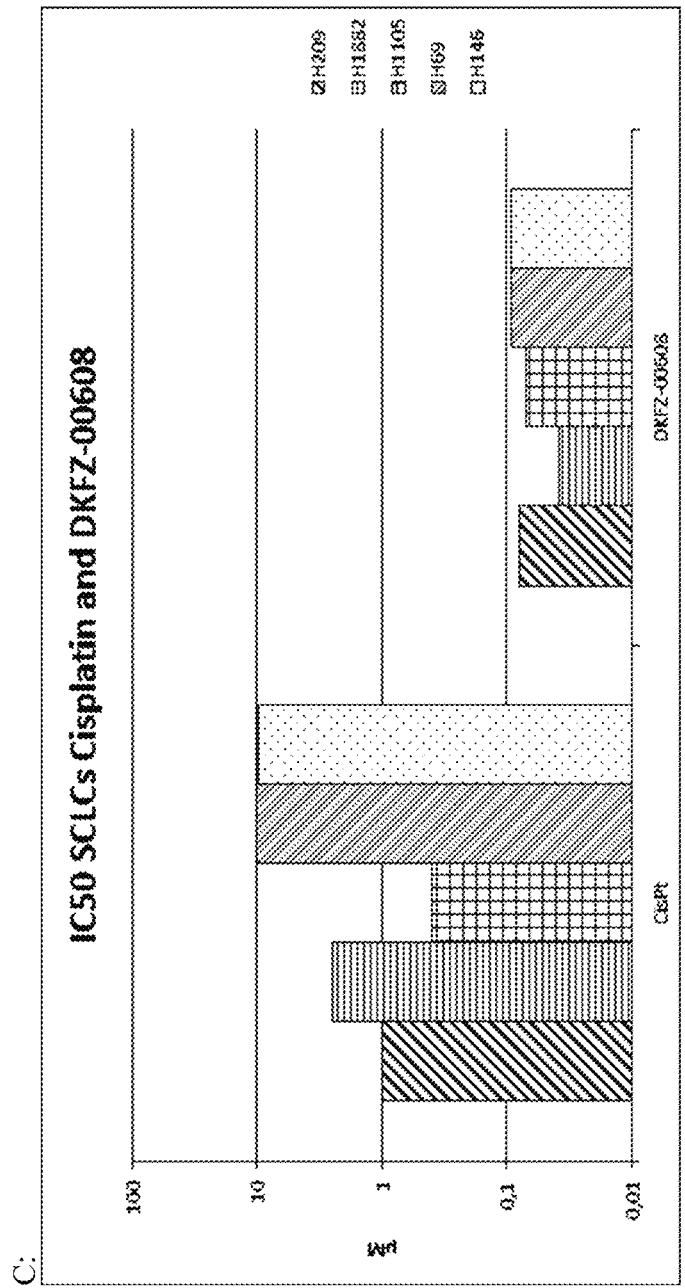

FIG. 8: shows the relative selectivity and resistance of DKFZ-00608 and Cisplatin in various SCLC cell lines.

Figure 9:
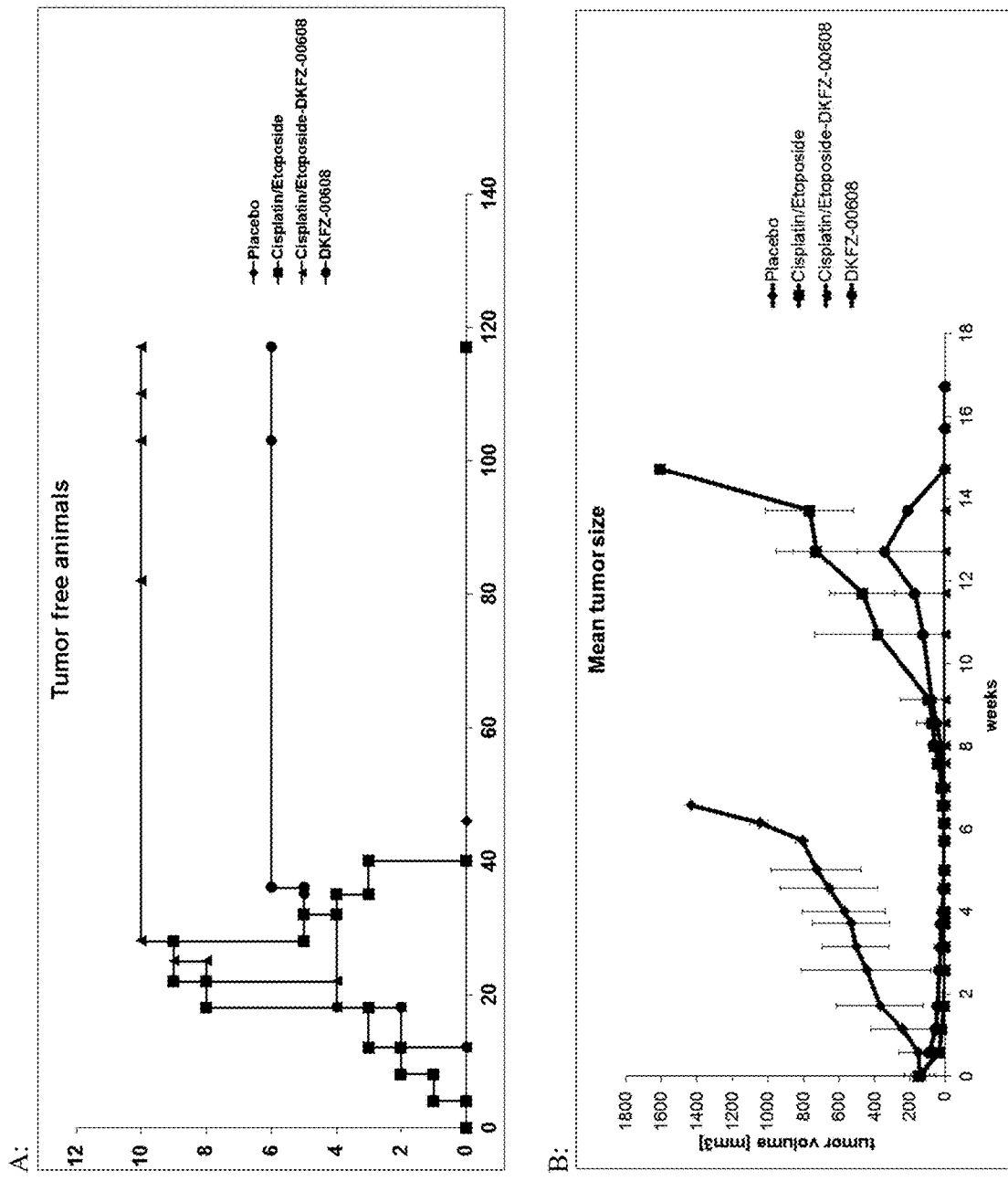
Figure 9:
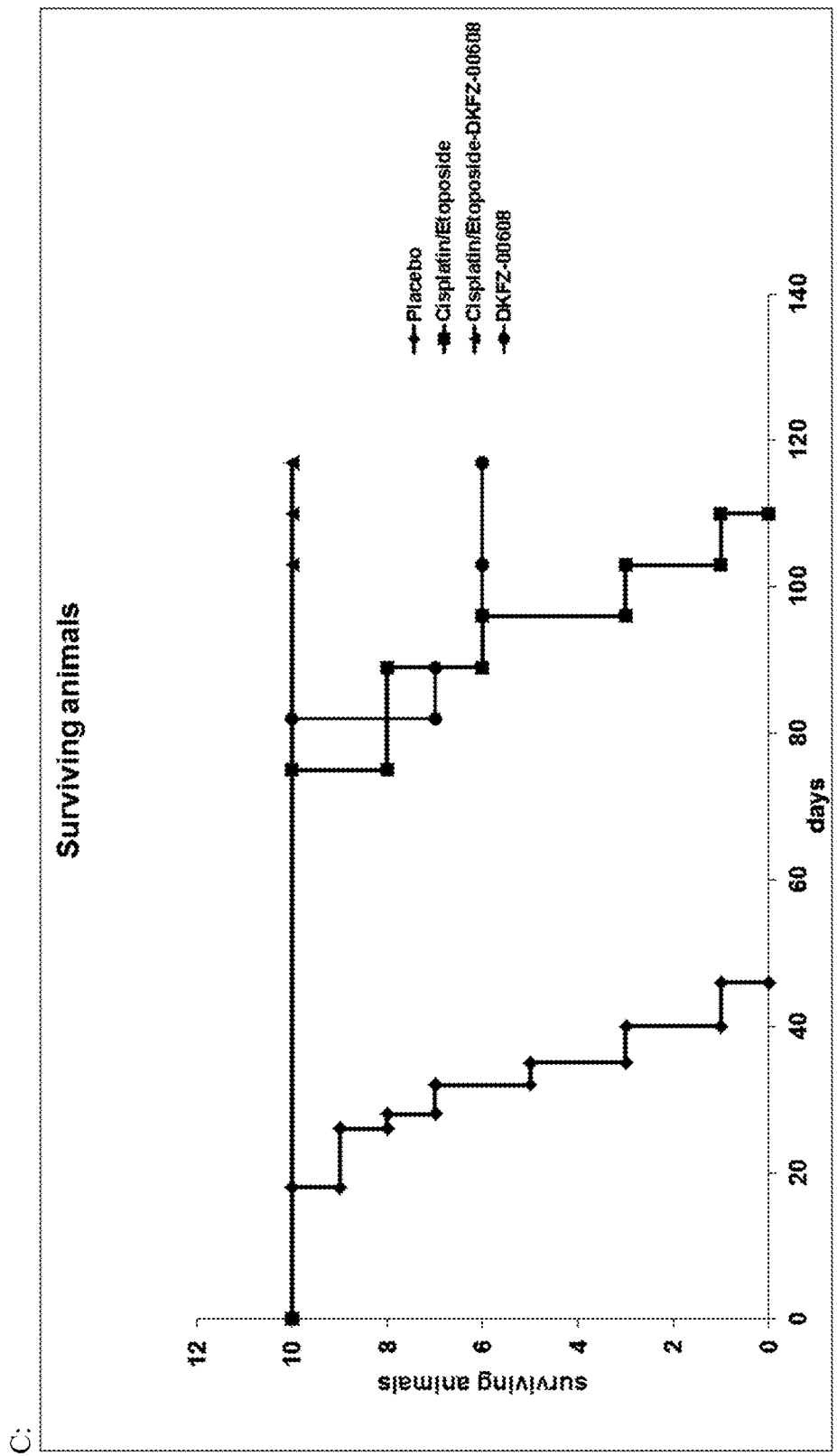

FIG. 9: shows anti-tumor activity of DKFZ-00608. A: tumor free animals over time; B: mean tumor size in animals; C: number of surviving animals.

EXAMPLES

Example 1: Cyclodextrin Stimulates the Anti-Tumor Effect of Combinations of Disulfiram with Various Heavy Metal Salts Jurkat T-cell leukemia cells were seeded in 96 well plates ($3\times10^4$/well). 24 h later cells were treated with disulfiram+ metal (ratio 1:1) in the presence or absence of hydroxypropyl-beta-cyclodextrin at a 30 fold molar ratio at various concentrations (10, 3.33, 1.11, 0.37, 0.123, 0.041, 0.014, 0.0 µM). In addition, cells were treated with cyclodextrin alone (1500, 500, 166.7, 55.56, 18.5, 6.17, 0.0 µM). All concentrations were tested in triplicate. After incubation at 37° C. for 72 h, Cell-titer-blue (Promega) was added (10 µl/well). After incubation at 37° C. for 4 h, fluorescence (excitation filter: 550 nm, emission filter 590 nm) was determined in an Optima ELISA reader. Mean values were calculated for each triplicate and IC50ies were calculated from non-fitted dose response curves.

"Normalized IC50 concentrations of metals" were calculated for each metal combination by dividing ICies (in the presence or absence of cyclodextrin) through the IC50 of cells treated with disulfiram+metal in the absence of cyclodextrin.

"Normalized IC50 of cyclodextrin" was determined for each metal combination by dividing the actual IC50 through the IC50 of cyclodextrin alone.

"Combination index" (CI) was calculated by the addition of "Normalized IC of cyclodextrin" and "Normalized IC50 concentrations of metals".

Results as Displayed in FIG. 1:

For all three metals (Au, Pt and Cu) in the presence of cyclodextrin a normalized IC50 of <1 was found.

The normalized IC50 for the concentration of metals in the absence of cyclodextrin is according to the above definition.

A normalized IC50 of 1 in the presence of cyclodextrin would indicate that cyclodextrin has no effect.

A normalized IC50 of >1 in the presence of cyclodextrin would indicate that cyclodextrin has an antagonistic effect on the anti-tumor activity.

A normalized IC50 of <1 in the presence of cyclodextrin indicates that cyclodextrin enhances the anti-tumor effect.

Furthermore, a CI of <1 was found for all metals (Cu, Pt and Au). This indicates a synergistic interaction between cyclodextrin and all metal/disulfiram combinations.

Example 2: Synergistic Anti-Tumor Effect of Cyclodextrin with Disulfiram/Aurothiomalate 10 different human cancer cell lines were seeded in 96 well plates in RPMI medium, supplemented with 10% FCS and 1 Pen/Strep at a density of $2\times10^4$ cells/well. Disulfiram and aurothiomalate were added at a fixed ratio of 1:1 in the presence of variable concentrations of hydroxypropyl-beta-cyclodextrin and aurothiomalate+disulfiram (ratios aurothiomalate+disulfiram/hydroxypropyl-beta-cyclodextrin: 1:0.037-1:27) in various dilutions ($1-2^{-6}$). For normalization, aurothiomalate+disulfiram and hydroxypropyl-beta-cyclodextrin were tested alone in various dilutions ($1-2^{-6}$). All concentrations were applied in triplicate. After incubation at 37° C. for 72 h Cell-titer-blue (Promega) was added (10 µl/well). After incubation at 37° C. for 4 h fluorescence (excitation filter: 550 nm, emission filter 590 nm) was determined in an Optima ELISA reader. Mean values were calculated for each treatment and IC50ies were calculated from non-fitted dose response curves.

Normalized IC50: IC50ies were normalized to the IC50ies of single drugs by dividing the IC50ies of combinations through either the IC50 of aurothiomalate+disulfiram, or the IC50 of hydroxypropyl-beta-cyclodextrin.

CI=Normalized IC50 of aurothiomalate/disulfiram concentration+normalized IC50 of hydroxypropyl-beta-cyclodextrin concentration.

Mean CI: Mean values+standard deviation were calculated from CIs of all tumor lines.

Results as Shown in FIG. 2:

Surprisingly, the combination of disulfiram+aurothiomalate with cyclodextrin resulted in a synergistic increase of the anti-tumor effect at a ratio of disulfiram+aurothiomalate/cyclodextrin of 1:3, 1:9 and 1:27. The difference to a hypothetic additive effect (CI=1) is significant (Student's T-test (P<$1\times10^{-9}$, $1\times10^{-9}$, $1\times10^{-3}$ respectively).

Example 3: Synergistic Anti-Tumor Effect of Disulfiram and Aurothiomalate in the Presence of Cyclodextrin Human T-cell leukemia Jurkat cells were seeded in 96 well plates in RPMI medium (serum free) at a density of $6\times10^4$ cells/well. Disulfiram and aurothiomalate were added in the presence of hydroxypropyl-beta-cyclodextrin (30 fold concentration of disulfiram concentration) (at various ratios of aurothiomalate/disulfiram ($1:4^8$-$1:4^{-8}$) in various dilutions ($1$-$4^{-6}$). All concentrations were applied in triplicate. After incubation at 37° C. for 72 h, Cell-titer-blue (Promega) was added (10 µl/well). After incubation at 37° C. for 4 h, fluorescence (excitation filter: 550 nm, emission filter 590 nm) was determined in an Optima ELISA reader. Mean values were calculated for each triplicate and IC50ies were calculated from non-fitted dose response curves. IC50ies were normalized to the IC50ies of single drugs.

Results as Shown in FIG. 3A:

The line of "additive effect" indicates the IC50ies that would be expected, if both drugs acted additive. Data points below this line indicate synergism. Surprisingly, all data points are very close to the x and y axis. This indicates a very high degree of synergism over a broad dose range. In order to enhance resolution of the graphical presentation, the graph was redrawn and axis were transformed to a logarithmic scale (see FIG. 3B)

Results as Shown in FIG. 3B:

Data points located under and left of the line of "additive effect" indicate synergisms at this concentration of both drugs. Surprisingly, synergism was observed over a broad concentration range (500-1250 fold) of both compounds: aurothiomalate: Between 80 nM and 100 µM (1250 fold). Disulfiram: Between 20 nM and 10 µM (500 fold).

Results as Shown in FIG. 3C:

A CI of <1 indicates synergism. Furthermore, the CI indicates the factor by which the total dose of the combined drugs can be reduced as compared to the single drugs.

Surprisingly, at a ratio of aurothiomalate/disulfiram between 0.06 and 16 (>250 fold dose range) the CI was below 0.1, indicating a more than 10 fold increased efficiency. At the optimum ratio 0.25 a CI of 0.012 was found, indicating a 83 fold increase in activity.

Unexpectedly, in comparison to other cases of synergism, the effect was very robust in that a synergistic effect >10 was observed over 5 different ratios of drug combination.

Example 4: Spectrum of Anti-Tumor Activity of Aurothiomalate/Disulfiram in Cyclodextrin Formulation A panel of 35 human cancer cell lines (obtained from ATCC) and 2 normal cell cultures (human peripheral blood lymphocytes (PBL, obtained from Promocell, Heidelberg) and normal human skin fibroblast cells (obtained from G. Darai, University of Heidelberg)) were seeded in 96 well plates in RPMI medium supplemented with 10% fetal calf serum and 1% antibiotics (penicillin/streptomycin) at a density of $2\times10^4$ cells/well. 24 h later, disulfiram and aurothiomalate were added in the presence of hydroxypropyl-beta-cyclodextrin (30 fold disulfiram concentration) (at various ratios aurothiomalate/disulfiram: $1:4^3$-$1:4^{-4}$) in various dilutions ($1$-$2^{-7}$). All concentrations were applied in triplicate. After incubation at 37° C. for 72 h, Cell-titer-blue (Promega) was added (10 µl/well). After incubation at 37° C. for 4 h, fluorescence (excitation filter: 550 nm, emission filter 590 nm) was determined in an ELISA reader (Optima, BMG Labtec). Mean values were calculated for each treatment and IC50ies were calculated from non-fitted dose response curves.

Results as Shown in FIG. 4A:

All data points are located left below the "Additive Effect Line". This indicates, that synergism was obtained at all disulfiram/aurothiomalate ratios in cyclodextrin formulation in all tested cells.

The distance of data points from the "Additive Effect Line" was variable for different cell lines. The distance to the "Additive Effect Line" indicates the degree of synergism. The highest distance and thus the best synergism was found in T-cell leukemia cells and small cell lung cancer cells, the lowest in HeLa cells.

Synergisms between disulfiram and aurothiomalate can be observed in cyclodextrin formulation in all tested cells. This effect differs from one cell line to the other up to 4 orders of magnitude.

Results as Shown in FIG. 4B:

The center of the T-cell lymphoma/leukemia data point cloud (0.14/0.1 µM aurothiomalate/disulfiram (mean values of aurothiomalate or disulfiram concentrations of all data points of the cloud)) was found to be ca. 100-fold lower in both dimensions (aurothiomalate concentration and disulfiram concentration) than the center of the normal cell cloud (4/10 µM aurothiomalate/disulfiram (mean values of aurothiomalate or disulfiram concentrations of all data points of the cloud)).

Surprisingly, all 3 T-cell lymphoma/leukemia cell lines were approximately 100 fold more sensitive to cyclodextrin formulated aurothiomalate/disulfiram treatment than normal cells.

Results as Shown in FIG. 4C:

The center of the small cell lung cancer cell data point cloud (0.05/0.05 µM aurothiomalate/disulfiram (mean values of aurothiomalate or disulfiram concentrations of all data points of the cloud)) was found to be ca. 50-fold lower in both dimensions (aurothiomalate concentration and disulfiram concentration) than the center of the normal cell cloud (4/10 µM aurothiomalate/disulfiram (mean values of aurothiomalate or disulfiram concentrations of all data points of the cloud)).

Surprisingly, all 3 SCLC cell lines were approximately 100 fold more sensitive to cyclodextrin formulated aurothiomalate/disulfiram treatment than normal cells.

Results as Shown in FIG. 4D:

CI can be used for quantitative analysis of synergism. A CI of <0.1 indicates that the total amount of combined drugs needed to kill 50% of cells is at least 10-fold lower than when single drugs are used separately A CI of <0.1 can be considered as biologically significant.

A CI of <0.01 can be considered as biologically highly significant.

In normal cells mean CIs <0.1 were found at disulfiram/aurothiomalate ratios between 2-0.25.

In T-cell-lymphoma/leukemia cells mean CIs <0.01 were found at disulfiram/aurothiomalate ratios between 16 and 0.125.

The difference of CI, found in T-cell-lymphoma/leukemia cells and normal cells was statistically significant at disulfiram/aurothiomalate ratios of 8 and 16 (Student's T-test, p=0.02 and 0.039 respectively.

Surprisingly, the synergism between disulfiram and aurothiomalate in cyclodextrin formulation is approximately 10 fold higher in T-cell-lymphoma/leukemia cells and in SCLC cells as compared to normal cells.

TABLE 1

Tumor type specific effect of aurothiomalate/disulfiram
in relation to all tested cell

| Tumor type | Mean "Mean realtive IC50" | Standard deviation | Difference to "all tested cells" significant at |
|---|---|---|---|
| All tested cells | 1.00 | 0.00 | |
| T-cell lymphoma/leukemia | 0.09 | 0.02 | T-test: p < 2 × 10$^{-4}$ |
| Normal cells | 0.99 | 0.38 | |
| Colon | 0.85 | 0.40 | |
| Glioma | 1.10 | 0.64 | |
| Ovary | 2.42 | 1.42 | |
| SCLC | 0.014 | 0.0073 | T-test: p < 1 × 10$^{-6}$ |
| NSCLC | 2.19 | 0.75 | |
| Liver | 1.39 | | |
| Mamma | 0.68 | 0.41 | |
| Pancreas | 0.94 | 0.35 | |
| Cervix | 2.63 | 0.90 | |
| Melanoma | 1.23 | 0.68 | |
| Burkitt lymphoma | 1.09 | 0.36 | |
| Non-T-cell leukemia | 0.20 | 0.08 | T-test: p < 2 × 10$^{-4}$ |

"Mean IC50ies of all tested cells" were calculated for each tested aurothiomalate/disulfiram ratio.

"Relative IC50ies" were calculated by dividing IC50ies through "Mean IC50 of all tested cells" of the corresponding aurothiomalate/disulfiram ratio. "Mean relative IC50ies" were calculated for each cell line from all tested aurothiomalate/disulfiram ratios. "Mean Mean relative IC50ies" were calculated from all "Mean relative IC50ies" from each tumor type and from all human normal cells.

Results as Shown in Table 1:

The "Mean 'Mean relative IC50ies'" of NSCLC, cervix carcinoma and mamma carcinoma were determined as >2.

NSCLC, cervix carcinoma and mamma carcinoma cell lines tested here, are resistant to aurothiomalate/disulfiram treatment in cyclodextrin formulation.

The "Mean 'Mean relative IC50ies'" of T-cell lymphoma/leukemia, non-T-cell leukemia and SCLC were determined as 0.09, 0.2 and 0.37, respectively. The difference to all tested cells was significant (Student's T-test, p<2×10$^{-4}$).

Surprisingly, the tested T-cell lymphoma/leukemia carcinoma, non-T-cell leukemia and SCLC cells are hypersensitive to aurothiomalate/disulfiram treatment in cyclodextrin formulation.

The "Mean 'Mean relative IC50ies'" of all other tumor cell types and normal human cells ranged between 0.68 and 1.23.

The tested colon-, ovary-, liver-, mamma-, pancreas-tumors, melanomas, gliomas and Burkitt lymphomas are sensitive to aurothiomalate/disulfiram treatment in cyclodextrin formulation.

Example 5: Aurothiomalate/Disulfiram in Cyclodextrin Formulation Overcomes Resistance of Chemotherapy Surviving Tumor Cells 10 million HT29 human colon cancer cells were seeded in 175 ml Falcon flasks. 24 h later 10 µM Oxaliplatin was added. After 48 h incubation at 37° C. fresh medium was added. 48 h later cells were trypsinized and seeded in 96 well plates at a density of 2×10$^4$ cells per well. Human skin fibroblasts and untreated HT29 cells were seeded in 96 well plates at the same density. After 24 h incubation at 37° C., cells were treated in triplicates with 1:2 serial dilutions of Vincristin (starting concentration 1 µg/ml), Oxaliplatin (starting concentration 50 µg/ml), 5-FU (starting concentration 500 Doxorubicin (starting concentration 10 µg/ml) and disulfiram/aurothiomalate+10 fold concentration of hydroxypropyl-beta-cyclodextrin in 2 µM aurothiomalate. After incubation for 72 h at 37° C. 10$_1$1.1 Cell-titer-blue was added per well. After incubation at 37° C. for 4 h, fluorescence (excitation filter: 550 nm, emission filter 590 nm) was determined in an ELISA reader (Optima, BMG Labtec). Mean values were calculated for each treatment and IC50ies were calculated from non-fitted dose response curves.

Calculation of "Factor of Resistance":

For each treatment, IC50ies in normal human cells and IC50 in Oxaliplatin treatment surviving cells were divided through the IC50 found with the same treatment in unselected HT29 cells.

A factor of resistance >1 indicates "resistance".

A factor of resistance=1 indicates "no resistance".

A factor of resistance <1 indicates "hypersensitivity". Hypersensitivity is obtained with drugs that selectively kill tumor cells resistant to standard chemotherapy.

Results as Shown in FIG. 5:

When cells which had not been treated before, were tested, all chemotherapeutic standard drugs (Vincristin, Oxaliplatin, 5-FU, Doxorubicin) show selectivity for colon cancer cells as compared with normal human fibroblasts. IC50ies in tumor cells are at least 100-fold lower than IC50ies in fibroblast.

HT29 cells, which had survived Oxaliplatin treatment were resistant to all chemotherapeutic standard drugs (Vincristin, Oxaliplatin, 5-FU, Doxorubicin). The factor of resistance (IC50 in surviving cells/IC50 in untreated control cells) was found to be between >10 and >100.

HT29 cells, which had survived Oxaliplatin treatment, were found to be as sensitive to aurothiomalate/disulfiram in cyclodextrin formulation as untreated HT29 cells. The factor of resistance was <1 (0.71).

In contrast, normal human fibroblasts were found to be resistant to aurothiomalate/disulfiram in cyclodextrin formulation (factor of resistance >1000).

Surprisingly, disulfiram/aurothiomalate in cyclodextrin displays no cross resistance with standard chemotherapeutic agents. Therefore, disulfiram/aurothiomalate offers itself as a salvage therapy by killing efficiently chemotherapy surviving cancer cells.

Example 6: Superior Selective Activity of Homoleptic Au-DTC Complexes on T-Cell Leukemia The anti-tumoral efficacy of a panel of 7 different Au complexes, ATM/Disulfiram, the standard therapeutic Cisplatin and well known antitumoral CuDTC (see Table 2) was tested on Jurkat human T-cell leukemia and Raji human B-cell lymphoma cells. Cells were seeded in 96 well plates in RPMI medium supplemented with 10% fetal calf serum and 1% antibiotics (penicillin/streptomycin) at a density of 3×10$^4$ cells/well. 24 h later, test compound were added in the presence of sulfobutyl ether-β-cyclodextrin (30 fold disulfiram concentration) in various dilutions (100-0.01 µM). All concentrations were applied in triplicate. After incubation at 37° C. for 72 h, Cell-titer-blue (Promega) was added (10 µl/well). After incubation at 37° C. for 2-8 h, fluorescence (excitation filter: 550 nm, emission filter 590 nm) was determined in an ELISA reader (Optima, BMG Labtec). Mean values were calculated for each treatment and IC50ies were calculated from non-fitted dose response curves. The "Factor of Selectivity for T-cell Leukemia" was calculated by division of IC50 on Raji cells/IC50 on Jurkat cells. Results are shown in table 3 and FIGS. 6A and 6B.

TABLE 2
| tested compounds: | | |
|---|---|---|
| Structure | Name | CAS # |
| 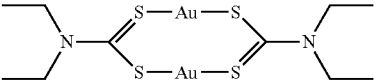 | DKFZ-00608 | 66712-10-5 |
| 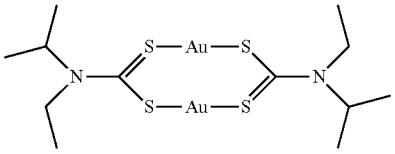 | DKFZ-00609 | |
| 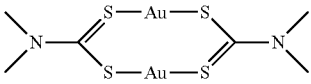 | DKFZ-00610 | 164363-66-0 |
| 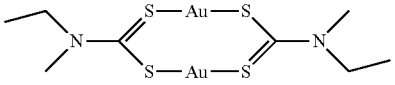 | DKFZ-00613 | |
| 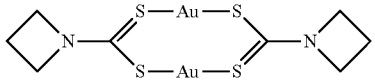 | DKFZ-00614 | |
| 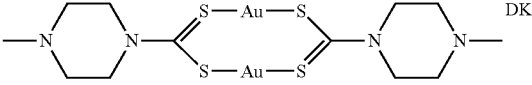 | DKFZ-00615 | |
| 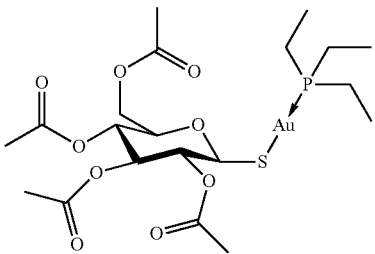 | Auranofin | 34031-32-8 |
| 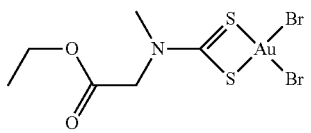 | AuL12 | 849802-92-2 |
| 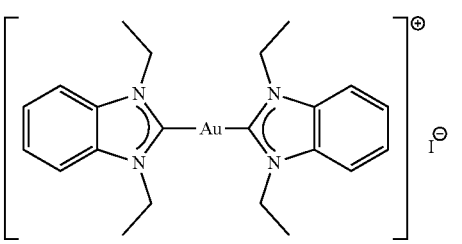 | MC3 | |
| 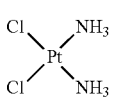 | Cisplatin | 15663-27-1 |
| 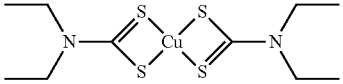 | CuDTC | 13681-87-3 |

TABLE 2-continued tested compounds:

| Structure | Name | CAS # |
|---|---|---|
| 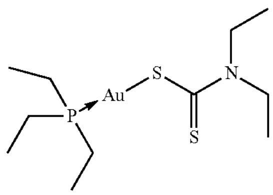 | P-A-uDTC | 889465-31 |

TABLE 3

IC50 (µM) of selected compounds of the Invention:

| Compound | Raji IC50 | Jurkat IC50 | selectivity for Jurkat IC50 Raji/IC50 Jurkat |
|---|---|---|---|
| AIM/Disulfiram | 16.98 | 0.11 | 153.31 |
| DKFZ-00608 | 32.66 | 0.05 | 635.70 |
| DKFZ-00609 | 26.80 | 0.10 | 275.09 |
| DKFZ-00610 | 24.57 | 0.28 | 86.67 |
| AuL12 | 51.90 | 25.64 | 2.02 |
| P-AuDTC | 0.51 | 0.07 | 6.87 |
| CuDTC | 0.02 | 0.01 | 2.62 |
| MC3 | 0.13 | 0.16 | 0.80 |
| Cisplatin | 2.72 | 0.61 | 4.45 |

In conclusion, the Au-dithiocarbamtes DKFZ-00608, DKFZ-00610 and DKFZ-00609 are highly active in Jurkat cells. IC50 of 50, 280 and 100 nM were found. Similarly, the mixture of ATM and Disulfiram and Cyclodextrin displayed and $IC_{50}$ of 110 nM. Further all Au-dithiocarbamtes DKFZ-00608, DKFZ-00610, DKFZ-00609 and the mixture of ATM and Disulfiram and Cyclodextrin were less active in Raji cells. A "Factor of Selectivity Results for T-cell Leukemia" of 635, 86.67, 275 and 153 was found respectively. All other complexes displayed a "Factor of Selectivity for T-cell Leukemia" of <10.

Example 7: Superior Selective Activity of Homoleptic Au DTC Complexes on SCLC Cells The anti-tumoral efficacy of a panel of 6 different Au complexes and the standard therapeutic of SCLC, Cisplatin was tested on 5 different human SCLC, three human NSCLC and the human non-tumorigenic cell line HaCat (results in FIG. 7). Cells were seeded in 96 well plates in RPMI medium supplemented with 10% fetal calf serum and 1% antibiotics (penicillin/streptomycin) at a density of 3×104 cells/well. 24 h later, test compound were added in the presence of sulfobutyl ether-β-cyclodextrin (30 fold disulfiram concentration) in various dilutions (100-0.01 µM). All concentrations were applied in triplicate. After incubation at 37° C. for 72 h, Cell-titer-blue (Promega) was added (10 µl/well). After incubation at 37° C. for 2-8 h, fluorescence (excitation filter: 550 nm, emission filter 590 nm) was determined in an ELISA reader (Optima, BMG Labtec). Mean values were calculated for each treatment and IC50ies were calculated from non-fitted dose response curves. Mean IC50ies+/−standard deviation (SD) were calculated for each test compound for SCLC and NSCLC lines. The "Mean Factor of Selectivity for SCLC versus NSCLC" was calculated by division of Mean IC50 on NSCLC cells/Mean IC50 on SCLC cells. The "Mean Factor of Selectivity for SCLC versus nontumorigenic cells" was calculated by division of IC50 on HaCat cells/Mean IC50 on SCLC cells. Results are shown in FIG. 7.

DKFZ-00608 was found to be the most active (lowest IC50) of all tested compounds. The IC50 was about 10 fold lower than that of all other tested non-AuDTC compounds in SCLC. For both AuDTC complexes a "Mean Factor of Selectivity for SCLC versus NSCLC" and a "Mean Factor of Selectivity for SCLC versus non-tumorigenic cells" of >100 was found. All other complexes showed lower selectivity ("Mean Factor of Selectivity for SCLC versus NSCLC" and "Mean Factor of Selectivity for SCLC versus non-tumorigenic cells" of <10.

Example 8: Lack of Cross Resistance of DKFZ-00608 with Cisplatin

A panel of 5 human SCLC lines was tested for sensitivity to Cisplatin and DKFZ-00608. Cells were seeded in 96 well plates in RPMI medium supplemented with 10% fetal calf serum and 1% antibiotics (penicillin/streptomycin) at a density of 3×104 cells/well. 24 h later, test compound were added in the presence of sulfobutyl ether-β-cyclodextrin (30 fold disulfiram concentration) in various dilutions (100-0.01 µM). All concentrations were applied in triplicate. After incubation at 37° C. for 72 h, Cell-titer-blue (Promega) was added (10 µl/well). After incubation at 37° C. for 2-8 h, fluorescence (excitation filter: 550 nm, emission filter 590 nm) was determined in an ELISA reader (Optima, BMG Labtec). Mean values were calculated for each treatment and IC50ies were calculated from non-fitted dose response curves. Relative IC50ies were calculated for each cell line by dividing the respective IC50/IC50 found in H209 cells. Results are shown in FIG. 8.

For DKFZ-00608 IC50ies between 38 and 95 nM were found. Relative IC50ies were of low variability. They were determined to be between 0.48 and 1.18. For Cisplatin high variability was found. IC50ies were found between 0.40 and 10.2 µM. Relative IC50ies were found between 0.4 and 10. Conclusion: There is no cross resistance between Cisplatin and DKFZ-00608 in SCLC cells.

Example 9: DKFZ-00608 Prevents Tumor Relapse after Cisplatin/Etoposide Treatment The inventors wanted to compare the efficacy of DKFZ-00608 on human SCLC tumors with standard therapy in vivo. Specifically the effect on tumor recurrence after successful treatment with Cisplatin/Etoposide, the major clinical complication in SCLC treatment, was of interest. Female nu/nu mice were injected with H209 SCLC cells (10×106 cell/mouse in 0.1 ml isotonic salt solution). After growth to a size of 0.08-0.12 mm³ groups of 10 animals were treated as follows:

Placebo daily for 9 weeks (60 mM sulfobutyl ether beta-cyclodextrin in isotonic salt solution).

Cisplatin (3 mg/kg once/week)+Etoposide (7.5 mg/kg twice/week) for 3 weeks.

Cisplatin (3 mg/kg once/week)+Etoposide (7.5 mg/kg twice/week) for 3 weeks. Followed by DKFZ-00608 in 60 mM sulfobutyl ether beta-cyclodextrin (15 mg/kg daily) for 6 weeks DKFZ-00608 in 60 mM sulfobutyl ether beta-cyclodextrin (15 mg/kg daily) for 6 weeks.

Tumor sizes were determined 2× per week for the first 9 weeks, thereafter, once per week.

Results are provided in FIG. 9A to 9C. All placebo tumors grew rapidly and all animals of this group had to be killed within 42 days. Cisplatin tumors regressed rapidly and after the end of treatment in 9/10 and 10/10 tumors were no longer palpable. Twenty days later in all animals re-growth of tumor was observed. When Cisplatin/Etoposide treatment was followed by DKFZ-00608 treatment reappearance of tumors could be prevented for at least 50 days. After 6 weeks treatment with DKFZ-00608, in 6 out of 10 animals no tumors were palpable. In 4 animals tumors had not completely regressed and resumed growth after termination of treatment, resulting in an increase of mean tumor size. After 82 days these tumors reached a size at which animals had to be euthanized. Only tumor free animals survived. Consequently, due to elimination of tumor bearing animals, the mean tumor size was falling again to 0 mm³. This explains the, upon first glance, paradox peak in the tumor size curve.

Hence, DKFZ-00608 treatment can prevent tumor relapse after initially successful standard therapy.

Example 10: Synthesis of the Compounds of the Invention

Synthesis of Au-DTC Complexes

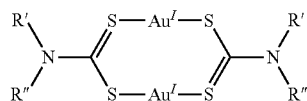

Where R' and R" are either connected resulting in a N-hetereocyclic ring system or linear/branched aliphatic carbon chains including hetereoatoms such as N, S, O, P, etc.

Preparation of Lithium Dithiocarbamate Salts:

The appropriate secondary amine was dissolved in dry THF and cooled to −78° C. An equimolar solution of n-butyllithium (2.5 M in hexane) was added dropwise to the solution and stirred for 15 minutes whereupon an equimolar amount of carbon disulfide was added. The resulting reaction mixture was stirred for 15 minutes at −78° C. and afterwards allowed to warm up to room temperature. After a total reaction time of 3 hours the solution was concentrated and dried under high vacuum over-night. The resulting off-white solid or oil (containing residues of THF) was used in the next step without further purification.

Preparation of Homoleptic Gold(I) Dithiocarbamate Complexes:

To an aqueous solution of aurothiomalate (ATM) or another gold(I) source dissolved in a suitable solvent, such as chloro(dimethyl sulfide)gold (I) in acetonitrile was added dropwise an ethanolic or aqueous solution of either an appropriate dithiocarbamate (dtc) salt (i.e. ammonia, alkali or alkaline earth metal salts, but preferably sodium or lithium) or an appropriate thiuram disulfide in a metal/dtc (or dithiuram) ratio of 1:1-2 at room temperature. While combining these solutions a yellow to orange colored precipitate formed. The suspension was stirred at room temperature overnight (or at least for 3 hours). Then the precipitate was purified by either filtering through a glass frit and subsequently washing with water, ethanol and diethylether or by centrifuging. With respect to the latter method the supernatant was taken away and the residue was resuspended in water and repeatedly centrifuged. The obtained solid was then dried under high vacuum overnight. If applicable this material was furtheron recrystallized using an appropriate organic solvent or solvent mixture preferably dimethylformamide, 1,2-dichloroethane or dichloromethane/hexane.

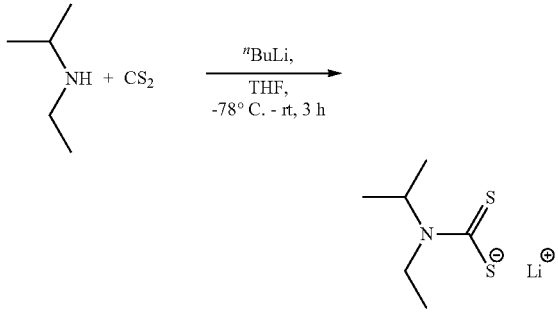

MM-VI-81

Chemical Formula: C$_6$H$_{12}$LiNS$_2$

Lithium N-ethyl, N-isopropyldithiocarbamate was synthesized according to the general procedure using 8.26 mmol of N-ethyl, N-isopropyl amine (0.72 g, 1.0 ml, 1 eq.), 8.26 mmol carbon disulfide (0.63 g, 0.5 ml, 1 eq.) and 8.26 mmol n-butyllithium (2.5 m in hexane, 4.67 ml, 1 eq.) in approximately 20.0 ml of dry THF. The product was obtained as an off-white solid in quantitative yield $^1$H NMR (400 MHz, D$_2$O) δ 5.86 (hept, J=6.8 Hz, 1H), 3.90 (q, J=7.1 Hz, 2H), 1.28 (t, J=7.0 Hz, 3H), 1.20 (d, J=6.8 Hz, 6H).

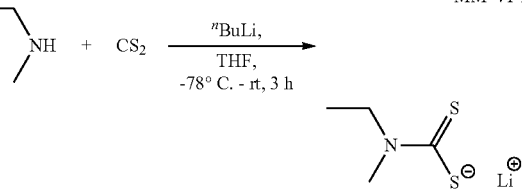

MM-VI-109

Chemical Formula: C$_4$H$_8$LiNS$_2$

Lithium N-ethyl, N-methyldithiocarbamate was synthesized according to the general procedure using 11.67 mmol of N-ethylmethyl amine (0.69 g, 1.0 ml, 1 eq.), 11.67 mmol carbon disulfide (0.89 g, 0.7 ml, 1 eq.) and 11.67 mmol n-butyllithium (2.5 m in hexane, 4.67 ml, 1 eq.) in approximately 50.0 ml of dry THF. The product was obtained as a reddish solid in quantitative yield.

$^1$H NMR (400 MHz, D$_2$O) δ 4.09 (q, J=7.2 Hz, 2H), 3.45 (s, 3H), 1.21 (t, J=7.2 Hz, 3H).

MM-VI-106

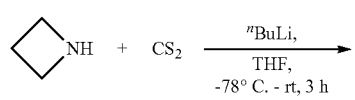

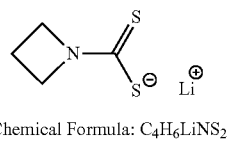

Chemical Formula: C$_4$H$_6$LiNS$_2$

Lithium azetidinedithiocarbamate was synthesized according to the general procedure using 14.89 mmol of azetidine (0.85 g, 1.0 ml, 1 eq.), 14.89 mmol of carbon disulfide (1.13 g, 0.9 ml, 1 eq.) and 14.89 mmol of n-butyllithium (2.5 M solution in hexane, 6.0 ml, 1 eq.) in approximately 50.0 ml of dry THF. The product was obtained as a white solid in quantitative yield $^1$H NMR (400 MHz, D$_2$O) δ 4.19-4.13 (m, 4H), 2.18-2.09 (m, 2H).

MM-VI-102

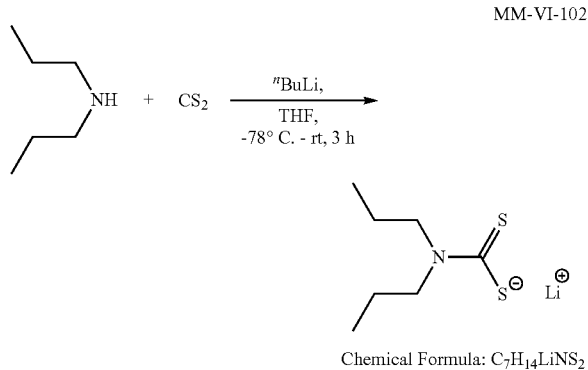

Chemical Formula: C$_7$H$_{14}$LiNS$_2$

Lithium di-n-propyldithiocarbamate was synthesized according to the general procedure using 10.97 mmol of dipropylamine (1.11 g, 1.5 ml, 1 eq.), 10.97 mmol of carbon disulfide (0.84 g, 0.66 ml, 1 eq.) and 10.97 mmol of n-butyllithium (2.5 M solution in hexane, 4.4 ml, 1 eq.) in approximately 20.0 ml of dry THF. The product was obtained as an off-white solid in quantitative yield.

$^1$H NMR (400 MHz, D$_2$O) δ 3.99-3.90 (m, 4H), 1.79-1.68 (m, 4H), 0.89 (t, J=7.5 Hz, 6H).

MM-VI-112

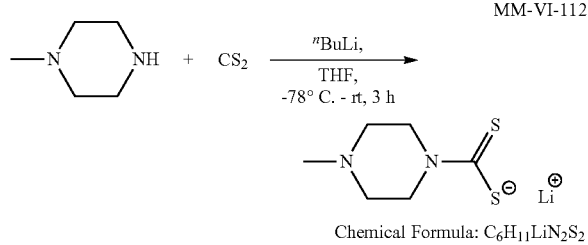

Chemical Formula: C$_6$H$_{11}$LiN$_2$S$_2$

Lithium 4-methylpiperazinyldithiocarbamate was synthesized according to the general procedure using 13.48 mmol of N-methylpiperidine (1.35 g, 1.5 ml, 1 eq.), 13.48 mmol of carbon disulfide (1.03 g, 0.81 ml, 1 eq.) and 13.48 mmol of n-butyllithium (2.5 M solution in hexane, 5.4 ml, 1 eq.) in approximately 20.0 ml of dry THF. The product was obtained as an off-white solid in quantitative yield.

$^1$H NMR (400 MHz, D$_2$O) δ 4.35 (br. s, 4H), 2.53 (br. s, 4H), 2.29 (s, 3H).

DKFZ-00616

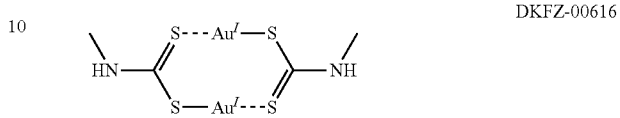

The complex [Au(N-methyl)dtc]n was synthesized according to the general procedure using 0.90 mmol of ATM (352.7 mg, 1.0 eq.) and 1.35 mmol of metam (174.4 mg, 1.5 eq.) predissolved in 10.0 ml of aqua dest. each. The obtained slightly greenish, yellow powder was thoroughly washed with water, small amount of ethanol and diethyl ether successively and dried under high vacuum over night. The product was obtained in a yield of 68% (183.6 mg, 0.61 mmol).

Elemental analysis: calcd C, 7.92; H, 1.33; N, 4.62; obsd C, 8.10; H, 1.49; N, 4.59.

DKFZ-00610

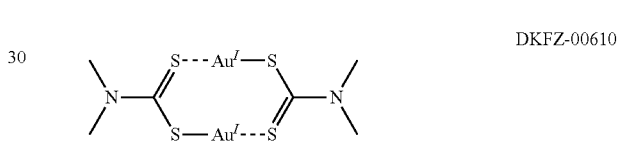

The complex [Au(N-dimethyl)dtc]n was synthesized according to the general procedure using 1.1 mmol of chloro(dimethyl sulfide)gold(I) (325.1 mg, 1.0 eq.) and 1.1 mmol of dimethyldithiocarbamate (157.5 mg, 1.0 eq.) predissolved in 20.0 ml of acetonitrile each. The obtained yellow powder was thoroughly washed with water, small amount of ethanol and diethyl ether successively and dried under high vacuum over night. The product was obtained as a yellow powder in a yield of 35% (121.8 mg, 0.38 mmol).

Elemental analysis: calcd C, 11.36; H, 1.91; N, 4.42; obsd C, 11.61; H, 2.00; N, 4.43.

DKFZ-00613

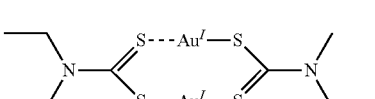

The complex [Au(N-ethyl, N-methyl)dtc]n was synthesized according to the general procedure using 1.35 mmol of ATM (527.0 mg, 1.0 eq.) and 2.03 mmol of the appropriate dithiocarbamate (286.6 mg, 1.5 eq.) predissolved in 10.0 ml of aqua dest. each. The obtained orange powder was thoroughly washed with water, small amount of ethanol and diethyl ether successively and dried under high vacuum over night. The crude product was obtained in a yield of 73% (327.6 mg, 0.99 mmol). This material was further purified by precipitation from hot 1,2-dichloroethane to afford a fluffy, orange colored solid as the pure product.

Elemental analysis: calcd C, 14.51; H, 2.43; N, 4.23; obsd C, 14.59; H, 2.66; N, 4.15.

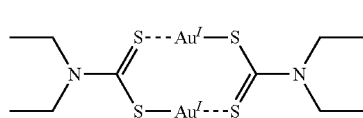

DKFZ-00608

The complex [Au(diethyl)dtc]n was synthesized according to the general procedure using 5.13 mmol of ATM (2.0 g, 1.0 eq.) dissolved in 100.0 ml of aqua dest. and 5.13 mmol of the tetraethyldithiuram disulfide (1.52 g, 1.0 eq.) dissolved in 100.0 ml of ethanol. The obtained orange powder was filtered and thoroughly washed with water and dried under high vacuum over night. This material was recrystallized from hot DMF to afford orange needles as the pure product in a yield of 68% (1.21 g, 3.50 mmol).

Elemental analysis: calcd C, 17.39; H, 2.92; N, 4.06; obsd C, 17.45; H, 3.02; N, 4.22.

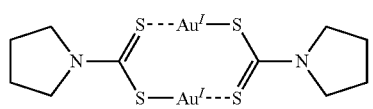

DKFZ-00617

The complex [Au(pyrrolidinyl)dtc]n was synthesized according to the general procedure using 1.03 mmol of ATM (400.0 mg, 1.0 eq.) and 2.05 mmol of the ammonium pyrrolidinedithiocarbamate (336.8 mg, 2.0 eq.) dissolved in 5.0 ml of aqua dest. each. The obtained orange powder was centrifuged. The supernatant was taken away and the residue was resuspended in water and again centrifuged (procedure repeated twice). The obtained orange solid was dried under high vacuum over night and afterwards recrystallized form hot DMF to afford orange-colored needles as the pure product in a yield of 38% (133.8 mg, 0.39 mmol).

Elemental analysis: calcd C, 17.50; H, 2.35; N, 4.08; obsd C, 17.73; H, 2.53; N, 4.23.

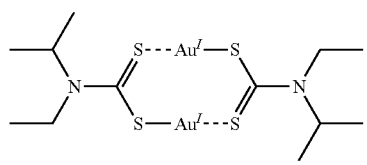

DKFZ-00609

The complex [Au(N-ethyl, N-isopropyl)dtc]n was synthesized according to the general procedure using 0.59 mmol of ATM (230.4 mg, 1.0 eq.) and 0.89 mmol of the lithium (N-ethyl, N-isopropyl)dithiocarbamate (150.0 mg, 1.5 eq.) dissolved in 10.0 ml of aqua dest. each. The obtained orange to brown powder was filtered and thoroughly washed with water. This material was recrystallized from chloroform/hexane affording dark-orange to brown crystals as the pure product in a yield of 19% (39.8 mg, 0.11 mmol).

Elemental analysis: calcd C, 20.06; H, 3.37; N, 3.90; obsd C, 19.61; H, 3.44; N, 3.80.

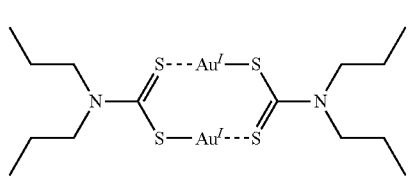

DKFZ-00612

The complex [Au(di-n-propyl)dtc]n was synthesized according to the general procedure using 1.23 mmol of ATM (478.0 mg, 1.0 eq.) and 1.84 mmol of the appropriate dithiocarbamate (337.1 mg, 1.5 eq.) predissolved in 10.0 ml of aqua dest. each. The obtained bright yellow powder was thoroughly washed with water, ethanol and diethyl ether successively. The crude product was obtained in a yield of 87% (400.9 mg, 1.07 mmol). Recrystallization from hot 1,2-dichloroethane afforded bright yellow needles as the pure product.

Elemental analysis (report 41176, [M]): calcd C, 22.52; H, 3.78; N, 3.75; obsd C, 22.31; H, 4.01; N, 3.64.

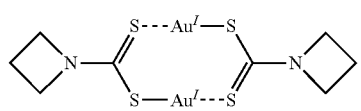

DKFZ-00614

The complex [Au(azetidinyl)dtc]$_n$ was synthesized according to the general procedure using 1.66 mmol of ATM (646.0 mg, 1.0 eq.) and 2.48 mmol of the appropriate dithiocarbamate (345.7 mg, 1.5 eq.) predissolved in 10.0 ml of aqua dest. each. The obtained bright yellow powder was thoroughly washed with water, small amount of ethanol and diethyl ether successively and dried under high vacuum over night. The product was obtained in a yield of 78% (427.9 mg, 1.30 mmol).

Elemental analysis: calcd C, 14.59; H, 1.84; N, 4.25; obsd C, 14.68; H, 2.24; N, 4.05.

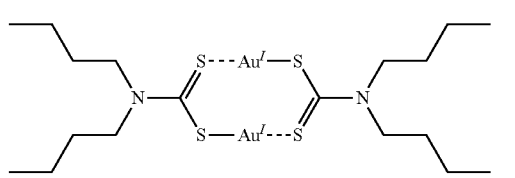

DKFZ-00618

The complex [Au(di-n-butyl)dtc]$_n$ was synthesized according to the general procedure using 1.04 mmol of ATM (407.5 mg, 1.0 eq.) predissolved in 10.0 ml of aqua dest. and 1.57 mmol of the appropriate sodium dithiocarbamate (aqueous solution, 45 wt %; 791.7 mg, 0.73 ml, 1.5 eq.). After stirring at room temperature over night the reaction mixture was extracted with chloroform (2×20 ml). The combined organic phases were washed with brine (1×20 ml), dried over MgSO$_4$ and concentrated. The residue was recrystallized from hot 1,2-dichloroethane to afford orange needles as the pure product in a yield of 35% (145.6 mg, 0.36 mmol).

Elemental analysis: calcd C, 26.93; H, 4.52; N, 3.49; obsd C, 26.83; H, 4.73; N, 3.30.

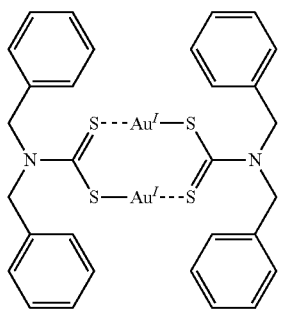

DKFZ-00611

The complex [Au(dibenzyl)dtc]$_n$ was synthesized according to the general procedure using 1.29 mmol of ATM (505.1 mg, 1.0 eq.) dissolved in aqua dest. and 1.94 mmol of the appropriate sodium dithiocarbamate (573.7 mg, 1.5 eq.) dissolved in 10.0 ml of methanol. The obtained bright yellow powder was thoroughly washed with water, small amount of ethanol and diethyl ether successively. The crude product was obtained in a yield of 64% (390.5 mg, 0.83 mmol). Recrystallization from chloroform/hexane afforded brown crystals as the pure product in a yield of 64% (390.5 mg, 0.83 mmol).

Elemental analysis (report 40981, [M]): calcd C, 38.38; H, 3.01; N, 2.98; obsd C, 38.31; H, 3.28; N, 2.86.

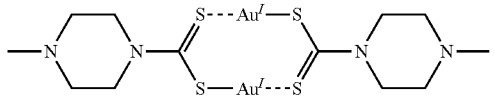

DKFZ-00615

The complex [Au(4-methylpiperazinyl)dtc]$_n$ was synthesized according to the general procedure using 1.29 mmol of ATM (502.0 mg, 1.0 eq.) and 1.93 mmol of the appropriate dithiocarbamate (351.7 mg, 1.5 eq.) predissolved in 10.0 ml of aqua dest. each. The obtained bright yellow powder was thoroughly washed with water, small amount of ethanol and diethyl ether successively. The crude product was obtained in a yield of 86% (414.8 mg, 1.11 mmol). Recrystallization from hot 1,2-dichloroethane afforded very fine, bright yellow needles as the pure product.

Elemental analysis (report 41228, [M]): calcd C, 19.36; H, 2.98; N, 7.53; obsd C, 19.42; H, 3.07; N, 7.85.

The invention claimed is:

1. A method for treating small cell lung cancer (SCLC) in a subject, comprising:
    administering an effective amount of a compound to the subject, the compound being selected from a complex according to the following formula (I):

(I)

wherein the $R_1$ and $R_2$ are the same or different, or are connected to form a N-heterocyclic 3- to 6-membered ring, and are selected from hydrogen, and unsubstituted or substituted $C_1$ to $C_{10}$ straight, branched or cyclic alkyl, unsubstituted or substituted $C_1$ to $C_{10}$ straight, branched or cyclic akenyl, unsubstituted or substituted aryl, and unsubstituted or substituted heteroaryl; and wherein M is Au;

or a diastereomer, enantiomer or a pharmaceutical acceptable salt thereof.

2. The method according to claim 1, wherein the compound is selected from any one of the following compounds:

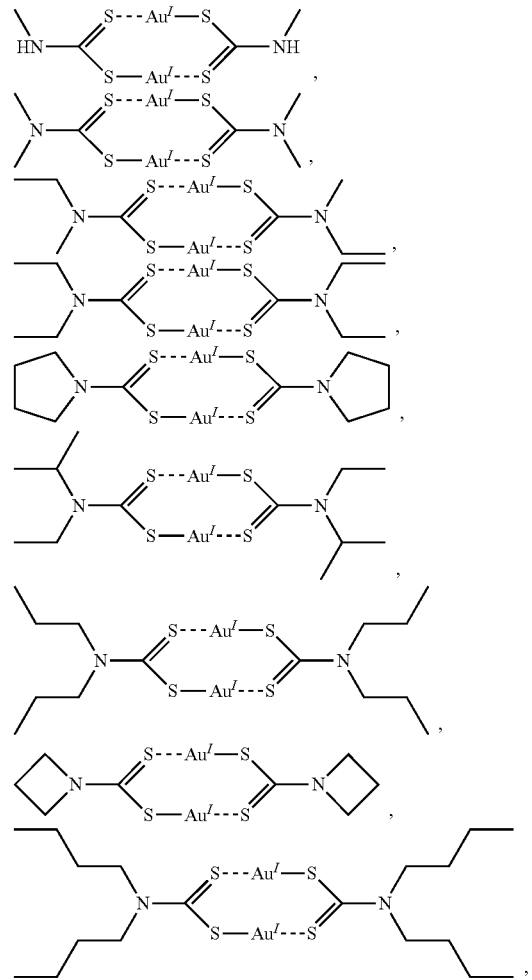

-continued

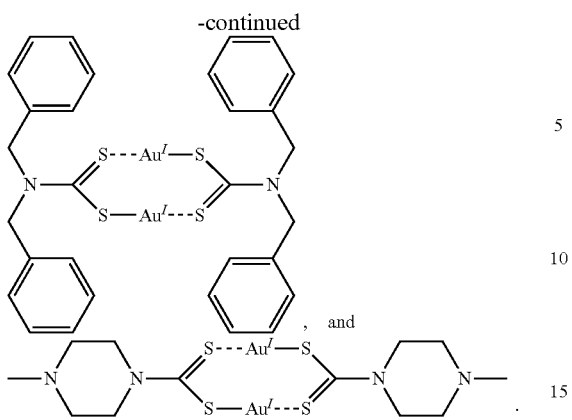

, and

3. The method according to claim 1, wherein the treatment comprises administration of the compound together with a cyclodextrin.

4. The method according to claim 1, wherein the compound according to claim 1 is administered as a pharmaceutical composition together with a cyclodextrin and a pharmaceutical acceptable carrier and/or excipient.

5. A method for treating small cell lung cancer (SCLC) in a subject, comprising:
administering an effective amount of a compound to the subject, the compound having any one of the following formulas:

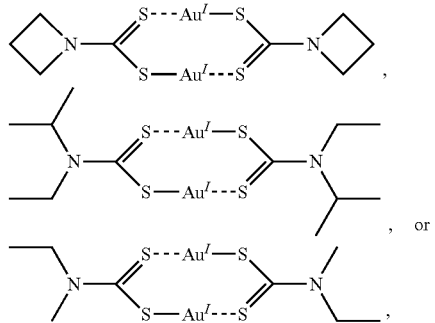

or a pharmaceutically acceptable salt thereof.

* * * * *